(12) United States Patent
Fisker et al.

(10) Patent No.: US 10,552,549 B2
(45) Date of Patent: Feb. 4, 2020

(54) VIRTUAL DESIGN OF ATTACHMENT OF DENTAL MODEL IN ARTICULATOR

(71) Applicant: 3Shape A/S, Copenhagen K (DK)

(72) Inventors: Rune Fisker, Virum (DK); Sven Nonboe, Hillerød (DK)

(73) Assignee: 3Shape A/S, Kobenhavn K (DK)

( * ) Notice: Subject to any disclaimer, the term of this patent is extended or adjusted under 35 U.S.C. 154(b) by 988 days.

(21) Appl. No.: 14/349,774

(22) PCT Filed: Oct. 5, 2012

(86) PCT No.: PCT/EP2012/069730
§ 371 (c)(1),
(2) Date: Apr. 4, 2014

(87) PCT Pub. No.: WO2013/050536
PCT Pub. Date: Apr. 11, 2013

(65) Prior Publication Data
US 2014/0242539 A1    Aug. 28, 2014

Related U.S. Application Data

(60) Provisional application No. 61/544,031, filed on Oct. 6, 2011.

(30) Foreign Application Priority Data

Oct. 6, 2011    (DK) .................. 2011 00774

(51) Int. Cl.
*G06F 17/50* (2006.01)
*A61C 11/00* (2006.01)
(Continued)

(52) U.S. Cl.
CPC ............ *G06F 17/50* (2013.01); *A61C 9/0046* (2013.01); *A61C 9/0053* (2013.01); *A61C 11/00* (2013.01);
(Continued)

(58) Field of Classification Search
CPC ....... A61C 11/00; A61C 11/08; A61C 11/085; A61C 13/0004; A61C 19/045;
(Continued)

(56) References Cited

U.S. PATENT DOCUMENTS 8,234,000 B2 * 7/2012 Andersson ........... A61C 9/0006
700/98
2004/0172150 A1 * 9/2004 Perot .................. A61C 13/0004
700/98
(Continued)

FOREIGN PATENT DOCUMENTS

DE    102009044147 A1    4/2011
WO    WO 2008/051130 A1    5/2008
WO    WO 2011/045680 A2    4/2011

OTHER PUBLICATIONS

International Search Report (PCT/ISA/210) dated Feb. 4, 2013, by the European Patent Office as the International Searching Authority for International Application No. PCT/EP2012/069730.
(Continued)

*Primary Examiner* — Aniss Chad
(74) *Attorney, Agent, or Firm* — Buchanan Ingersoll & Rooney PC

(57) ABSTRACT

A method for virtually designing the attachment of a manufactured dental model of a patient's set of teeth in a physical dental articulator by one or more kinds of spacer elements, where the method includes obtaining a virtual 3D dental model, providing a virtual dental articulator, where the height of the dental model is the height of an upper part and the height of a lower part of the dental model; providing one or more kinds of virtual spacer elements with predetermined heights, determining a manufacture height of the dental model and determining the number of each of the kinds of spacer elements to be used for the attachment of the manufactured dental model in the physical articulator, such that
(Continued)

the manufacture height of the dental model and the total effective spacer element height, equals the articulator height.

26 Claims, 24 Drawing Sheets

(51) Int. Cl.
*A61C 11/08* (2006.01)
*A61C 13/00* (2006.01)
*A61C 9/00* (2006.01)
*G16H 20/40* (2018.01)
*A61C 19/045* (2006.01)

(52) U.S. Cl.
CPC ............ *A61C 11/08* (2013.01); *A61C 11/085* (2013.01); *A61C 13/0004* (2013.01); *A61C 19/045* (2013.01); *G16H 20/40* (2018.01)

(58) Field of Classification Search
CPC ..... A61C 9/0046; A61C 9/0053; G06F 17/50; G16H 20/40
See application file for complete search history.

(56) References Cited

U.S. PATENT DOCUMENTS

| | | |
|---|---|---|
| 2005/0250075 A1 | 11/2005 | Taub et al. |
| 2008/0286722 A1 | 11/2008 | Berckmans, III et al. |
| 2009/0111071 A1 | 4/2009 | Yau et al. |
| 2009/0149977 A1 | 6/2009 | Schendel |
| 2010/0191510 A1 | 7/2010 | Kopelman |
| 2011/0191081 A1* | 8/2011 | Malfliet ................ A61C 11/00 703/11 |
| 2011/0276159 A1 | 11/2011 | Chun et al. |
| 2012/0295219 A1 | 11/2012 | Monteiro Geras et al. |
| 2013/0066598 A1* | 3/2013 | Fisker ................... A61C 11/00 703/1 |

OTHER PUBLICATIONS

Office Action (Summons to Attend Oral Proceedings) dated Oct. 30, 2018, by the European Patent Office in corresponding Europeane Patent Application No. 12768851.3. (9 pages).

\* cited by examiner

Fig. 2)

Fig. 16
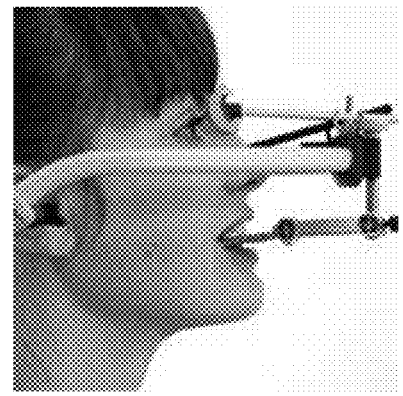
a)
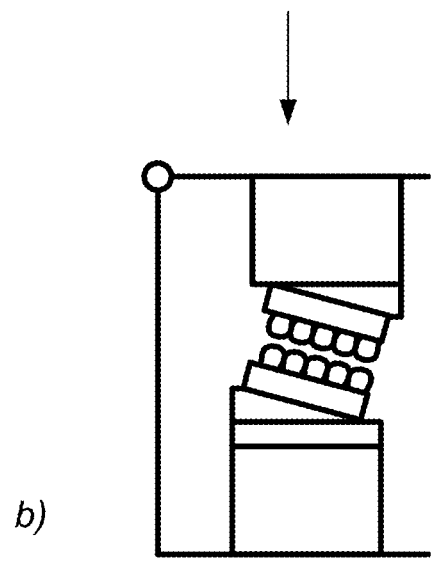
b)
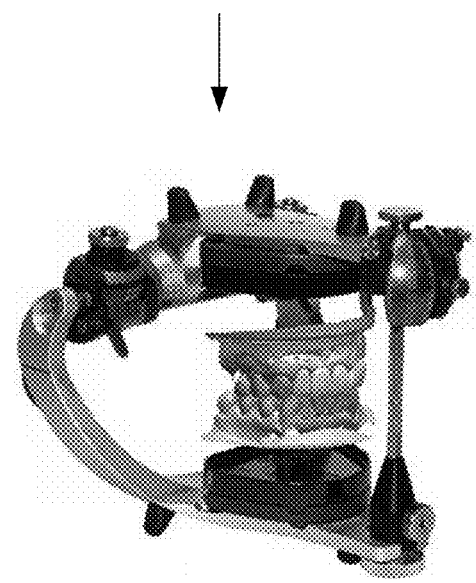
c)

a)

b)

c)

VIRTUAL DESIGN OF ATTACHMENT OF DENTAL MODEL IN ARTICULATOR

FIELD OF THE INVENTION

This invention generally relates to a method, system and kit for virtually designing the attachment of a manufactured dental model of a patient's set of teeth in a physical dental articulator. More particularly, the invention relates to designing the attachment by means of spacer elements.

BACKGROUND OF THE INVENTION

US2005250075A discloses a method for creating a physical teeth model comprising: providing a virtual three dimensional (3D) representation of a patient's dentition that comprises at least a region of the teeth that includes a tooth stump on which a crown is to be fitted or a region on to which a bridge is to be fitted; and preparing a physical model of the jaws of a subject from a blank, based on information from said virtual 3D image, wherein said physical model is a positive model comprises two members, one representing the upper jaw and the other the lower jaw, both members are produced with an alignment arrangement to permit proper occlusion alignment of the two members, and wherein the alignment arrangement includes a mounting arrangement for mounting said members on an articulator.

WO11045680A discloses a dental articulator for positioning the arcades without the use of plaster, being characterized by a equipment that includes a support structure (1), a superior positioning/repositioning set (2) an inferior positioning/repositioning set (2a), tilting sets (17, 17a), a lateral-frontal motion set (80), arm movement (9), support plates of plaster models of the arches (3), protractor (4), horizontal rod (5), a positioning/repositioning set of the arc (7) and stem with bite fork (8), the support structure (1) comprises a cover (10), supported on two lateral structures (13) which in turn are supported throughout the lower base (12) and the whole of the lower base (12) comprises means for mandibular movement.

US2010191510A discloses that tooth models can be designed in a virtual manner starting with a first virtual model, and then adding to this model, in a virtual sense (i.e., within the computer environment of computer system 260 or another computer system), virtual representations of the mounting blocks 30, the particular geometry of each mounting block being designed such as to displace and/or rotate the first virtual model in up to six degrees of freedom so that the cusp tip plane thereof is in the correct relationship to the hinge axis AH when mounted to a geometry as defined by the arms, hinge and mounting arrangement 60 of the particular articulator 10.

It remains a problem to provide a method and system for virtually designing the arrangement of a dental model in an articulator by means of spacer elements.

SUMMARY

Disclosed is a method of virtually designing the attachment of a manufactured dental model of a patient's set of teeth in a physical dental articulator by means of one or more kinds of spacer elements, where the method comprises:
obtaining a virtual 3D dental model of the patient's set of teeth, where the virtual 3D dental model is provided by means of 3D scanning;
providing a virtual dental articulator type corresponding to a physical dental articulator, where the dental articulator comprises an upper and a lower arm and has a known articulator height, which is the distance between the upper arm and the lower arm in the static position of the dental articulator;
providing a minimum height of the dental model, where the height of the dental model is the height of an upper part and the height of a lower part of the dental model;
providing one or more kinds of virtual spacer elements with predetermined heights, where each kind of virtual spacer element corresponds to a physical spacer element;
determining a manufacture height of the dental model and determining the number of each of the kinds of spacer elements to be used for the attachment of the manufactured dental model in the physical articulator,
such that the manufacture height of the dental model and the total effective spacer element height, which is the added height of the determined spacer elements, equal the articulator height, and where the manufacture height of the dental model is not less than the minimum height of the dental model.

Consequently, it is an advantage that the height of the dental model and the number of each kind of spacer elements are determined such that the height of the manufactured dental model is adapted to be minimized in the manufacturing process, while ensuring that the height of the manufactured dental model and the total effective height of the number of each kind of spacer elements equal the height between the upper arm and the lower arm of the dental articulator.

Furthermore, it is an advantage that an optimal height of the dental model can be determined such that the height of the model base can be minimized for reducing the amount of material to be manufactured when producing the dental model. If the manufacturing of the dental model is by means of printing, the printing material can be reduced, which is an advantage, because the printing material is expensive. If the manufacturing is by means of milling, the thickness of the blank can be reduced, so that both the material usage can be reduced and time and money can be saved since as little material as possible should be milled out of the blank, when the height of the dental is minimized, and milling is both time-consuming and therefore expensive.

Furthermore it is an advantage that an optimal number of each kind of the one or more spacer elements can be determined, such that when combining the determined one or more spacer elements and the determined manufacture height of the manufactured dental model, the manufactured dental model is suitable for attachment in any type of or any brand of physical dental articulators, while the production of the dental model requires as little manufacturing as possible.

Furthermore it is an advantage that gypsum is not needed for attaching the dental model, because the dental model can be attached exclusively by means of spacer elements instead, since the height of the dental model and the total effective height of the determined spacer elements equal the height of the dental articulator, which is the distance between the upper arm and the lower arm of the dental articulator. However, gypsum may still be used together with the spacer elements, such that less spacer elements are required for attaching the dental model on the articulator, if the user prefers also using gypsum.

A dental model may for example have a height of 30 mm. If the height can be reduced, printing material can be reduced. Just a few millimeters reduction in height of the dental model, can be a great advantage when printing a dental model, both in terms of material savings and time savings, and it is therefore a cost advantage to reduce the height or thickness of the dental model.

A spacer element may for example have a height of 5 mm, so if the height of the dental model can be reduced with 5 mm, then an additional spacer element can be used for the attachment of the dental model whereby manufacturing material for the dental model is reduced. The spacer elements will typically be pre-manufactured, reusable elements, which is used again and again with different dental models. So there will be no extra cost for the dental lab when using more spacer elements for attaching the dental model in the articulator, since the dental lab will typically have a number of spacer elements available.

If the spacer elements are produced for the specific dental model, such as spacer elements with inclined surfaces with a specific angle for retaining a dental model which is to be arranged with the specific angle relative to the horizontal plane of the articulator, then the spacer elements may be produced in a cheaper material than the material of the dental model, or the spacer elements may be produced by a faster method than the method for producing the dental model, and it will thus also be an advantage to reduce the height and the material use of the dental model, because the production of a high spacer element or of many spacer elements may still be cheaper than the production of a higher dental model.

In the case where the spacer elements can be produced for the specific dental model, the predetermined heights of the spacer elements can be any height with the manufacture precision or accuracy in height which is possible for the machine which shall manufacture the spacer elements. Some machines may for example have an accuracy in height of the produced items, which is 2 mm, 1.0 mm, 0.50 mm or the like. The predetermined height of a spacer element can then be 14 mm, 14.0 mm, 14.00 mm etc.

The articulator height is the distance between the upper and lower arm of the articulator. The distance may be the internal distance, i.e. the shortest distance between the arms, such as the distance from the side of one of the arms pointing towards the closest side of the other arm.

The effective total height of the spacer elements is such that the determined spacer elements retain the dental model in the articulator.

Thus the effective total height of the spacer elements is configured for retaining or securing the dental model in the articulator, because the effective total height of the spacer elements corresponds to the difference between the articulator height and the manufacture height of the dental model.

Thus the total effective height of the spacer elements causes that the dental model is retained by the spacer elements in the articulator, because the distance between the articulator arms, which is the articulator height, subtracted the height of the dental model is equal to the effective spacer element height.

Thus in some embodiments the effective height of the spacer elements is the height of the spacer elements which is configured for retaining the manufactured dental model in the articulator.

The upper part of the dental model represents the patient's upper jaw/teeth and the lower part of the dental model represents the patient's lower jaw/teeth.

The upper part of the manufactured dental model is adapted to be connected to the upper arm of the physical dental articulator, and the lower part of the manufactured dental model is adapted to be connected to the lower arm of the physical dental articulator.

Scanning an object in a 3D scanner for obtaining a three dimensional representation of the surface of the object can also be denoted 3D modeling, which is the process of developing a mathematical representation of the three-dimensional surface of the object via specialized software. The virtual or digital product may be called a 3D model. A 3D model represents the 3D object using a collection of points in 3D space, connected by various geometric entities such as triangles, lines, curved surfaces, etc. The purpose of a 3D scanner is usually to create a point cloud of geometric samples on the surface of the object.

3D scanners collect distance information about surfaces within its field of view. The "picture" produced by a 3D scanner describes the distance to a surface at each point in the picture.

Determination of the Manufacture Height of the Dental Model and Spacer Elements

In some embodiments determining the manufacture height of the dental model and determining the number of each of the kinds of spacer elements to be used for the attachment of the manufactured dental model in the physical articulator comprises:
- determining if any combination of spacer elements provides the difference between the articulator height and the minimum height of the dental model;
  - if yes, then the difference between the articulator height and the minimum height of the dental model is the total effective spacer element height, and the manufacture height of the dental model is equal to the minimum height of the dental model;
  - if no, then based on the predetermined heights of the one or more kinds of spacer elements determine a possible total effective spacer elements height, and then determine the manufacture height of the dental model as the difference between the articulator height and the possible total effective spacer elements height, whereby the manufacture height of the dental model is larger than the minimum height of the dental model.

It is an advantage to determine whether any combination of spacer elements provides the difference between the articulator height and the minimum height of the dental model, because since the spacer elements have predetermined heights, then the height of the dental model should be adjusted to fit the steps which the height of the spacer elements can be modified in. Thus if the smallest spacer element height is 1 mm high, and 0.5 mm is still needed for filling out the rest of the space between the dental model and the articulator after already having added one or more spacer elements, then no more spacer elements can be added, since this would make the total effective spacer element height 0.5 mm to high. The solution can then be to design the dental model to be 0.5 mm higher instead. Alternatively if the dental model can be manufactured to be 0.5 mm lower, then the dental model should be manufactured 0.5 mm lower and then the spacer element with a height of 1 mm can be used also.

The dental model may be manufactured by a digital 3D manufacturing technique such as printing, milling, sintering etc. For example when printing a dental model, there may also be restrictions in the height of the dental model since the printing of the model may comprise adding layers of material, and if a layer has a minimum thickness, then this may also be taken into consideration and accounted for when designing the height of the dental model and the total effective height of the dental model.

In some embodiments the manufacture height of the dental model and the total effective spacer element height are determined by an iterative process, where the manufacture height of the dental model and the total effective spacer element height are alternately adjusted in steps.

It is an advantage that for each adjusted total effective spacer element height, the computer software or the operator/user may test whether any combination of the individual spacer elements with the predetermined heights can provide the adjusted total spacer element height. If no combination of spacer elements satisfy the selected total effective spacer elements height, then a new total effective spacer elements height can be selected and tested etc.

Total Effective Spacer Element Height

In some embodiments a number of different possible total effective spacer element heights are determined based on the predetermined heights of the spacer elements.

The different possible total effective spacer elements heights can for example be determined before the method is performed, so that the possible total spacer elements heights are known in advance and does not need to be calculated at the same time as the method is performed. If there are many different spacer elements heights, then the combination options are many, and it may take time to calculate all of them.

In some embodiments the highest possible total effective spacer element height is selected.

It is an advantage to select the highest possible total effective spacer element height, because then the manufacture height of the dental model will be the smallest possible.

Manufacture Height of Dental Model

In some embodiments the manufacture height of the dental model is configured to be determined by the manufacture method which is used for manufacturing the dental model.

It is an advantage because for example if the dental model is manufactured by means of 3D printing, the layer height which the dental model is printed in, may be a part of the determination of the manufacture height of the dental model, since the dental model may only be printed in certain heights corresponding to the layer height.

Likewise if the dental model is manufactured by milling a blank, the blanks may be produced in certain heights, and it may then be an advantage that the manufacture height of the dental model fit or match the possible heights of the blank. The manufacture height of the dental model may then be equal to the height of the blank, so that as little material should be milled away from the blank. Since a dental model will have the shape of teeth, which are not flat but curved and irregular, the height of the model will vary at different points on the surface, and thus the height is not constant for the entire dental model. The highest point on the dental model may define the height of the dental model. In case of milling, the highest point on the dental model may correspond to the height or thickness of the blank.

In some embodiments the total effective spacer element height is determined such that the manufacture height of the dental model is as close to the minimum height of the dental model as possible.

In some embodiments the manufacture height of the dental is determined such that the manufacture height is as close as possible to the minimum height of the dental model.

It is an advantage that the manufacture height is as close as possible to the minimum height, since hereby as little material as possible is used when printing the dental model or as little material as possible should be milled away when milling the dental model from a blank.

In some embodiments the manufacture height of the dental model is determined such that the manufacture of the dental model is configured to require as little material use as possible.

It is an advantage that as little material as possible is required for the manufacture of the dental model, as this will save cost, manufacturing time etc.

In some embodiments the manufacture height of the dental model is determined such that the manufacture of the dental model is configured to be performed as quickly as possible.

It is an advantage, since this will save manufacturing time.

Orientation of Dental Model

In some embodiments the method comprises providing the orientation of the 3D virtual dental model in the virtual articulator corresponding to the orientation which the manufactured dental model is intended to be arranged with in the physical dental articulator. The 3D virtual dental model may then be arranged in the virtual articulator according to the orientation which the manufactured dental model is intended to be arranged with in the physical dental articulator.

It is an advantage that the orientation of the 3D virtual model is provided, such that the virtual orientation of the 3D model in the virtual articulator corresponds to the physical orientation that the 3D manufactured model is intended to have in the physical articulator, since hereby the orientation of the 3D model may correspond to the patient's actual mouth, jaw and bite anatomy or physiology, and this is an advantage when the occlusion of the patient shall be tested or checked in the articulator.

In some embodiments the orientation of the 3D virtual dental model in the articulator comprises the angle of the occlusion plane of the 3D virtual dental model relative to the horizontal plane in the virtual dental articulator corresponding to the angle of the occlusion plane of the manufactured dental model relative to the horizontal plane of the physical dental articulator which the manufactured dental model is intended to be arranged with in the physical dental articulator.

It is an advantage since the angle of the occlusion plane of the 3D dental model relative to the horizontal plane of the dental articulator may determine the orientation of the 3D dental model in the articulator.

Alternatively this may be described as the angle of the occlusion plane of the 3D virtual dental model relative to the horizontal plane of the virtual articulator.

The occlusal plane may be defined as a plane passing through the occlusal or biting surfaces of the teeth, and it may represent the mean of the curvature of the occlusal surface. Occlusal plane may also be called biteplane.

In some embodiments the method comprises that if the angle of the occlusal plane of the dental model is corresponding to the horizontal plane of the articulator, the dental model is arranged with no inclination in the articulator, and the total effective height of the spacer elements is then the actual height of the spacer elements when arranged for retaining the dental model in the articulator.

This discloses the situation where the angle of occlusal plane is horizontal, i.e. with no inclination or no angle relative to the horizontal. Some patient's may really have this angle of the occlusal plane, or this angle may be selected by the dentist and/or by the dental technician and/or by the type of articulator used, as it may be easy to use a horizontal occlusal plane instead of using an inclined occlusal plane.

In the cases where the angle of the occlusal plane of the dental model is different from the horizontal plane of the articulator, the dental model is arranged with an inclination in the articulator, and the total effective height of the spacer elements may be calculated as the actual height of the rectangular shaped spacer elements and as the added height of triangular shaped spacer elements when these are arranged in space to form a rectangular shaped unit. Determining the manufacture height of the dental model and the number of each of the kinds of spacer elements to be used for the attachment of the dental model in the physical articulator should then be based on a projected height of the dental model, which is the projection of the height onto a vertical axis of the dental articulator.

If some of the spacer elements comprise an inclined side such as a triangular shaped spacer element for attaching a dental model in the articulator with an inclination, then there may be two triangular shaped spacer elements, one for each part of the dental model, and the effective height of the two triangular shaped spacer elements may be the height obtained when the two triangular shaped spacer elements are arranged together as a rectangular box, e.g. it may be height of the highest of the two triangular shaped spacer elements, and/or it may be half the height of one of the triangular shaped spacer elements plus half the height of the other triangular shaped spacer element.

Thus in cases where there are two spacer elements with an inclined surface the height of the two spacer elements may be the same, and in this case only the height of one of the spacer elements is included in the total effective height of the spacer elements, or half the height of both inclined spacer elements may be included in the total effective height of the spacer elements. If the spacer elements comprise pins, then the effective height of the pins may be the highest column of pins for each of the two parts of the dental model, i.e. both the highest column of pins arranged in relation to the lower part of the dental model plus the highest column of pins arranged in relation to the upper part of the dental model.

Thus no matter how the shape, size, direction or spacious or spatially arrangement of the individual spacer elements are, the total effective height of the spacer elements is the height or distance or extent which the spacer elements are arranged in and which retains the dental model in the articulator when the articulator is in its static position, i.e. when the articulator is closed and the two jaws or upper and lower part of the dental model touches each other.

Stability of Dental Model

In some embodiments the minimum height of the dental model is determined based on stability criteria.

It is an advantage that the minimum height of the dental model is determined taking stability criteria into account, because there may be a lower limit for how low the dental model or one or both of the parts of the dental model may be, when the dental model or one or both of the parts should remain stable and robust.

In some embodiments the minimum height of the dental model is determined based on the type of preparation and/or based on the type of pin on the tooth preparation die and/or based on the support means fixing the tooth preparation die in the manufactured dental model.

It is an advantage because in order to obtain e.g. stability of the prepared tooth/teeth die in the dental model, the length of the die which may comprise the length of a potential base pin on the die extending into the base of the dental model, should maybe be of a certain length and/or width, such that the preparation die tooth can be firmly arranged in the dental model. If the die itself or the pin of the die is too short or too narrow, the die may not be able to be stable enough in the dental model. Therefore there may be a minimal height which the die and thereby the dental model can have in order for obtaining stability of the die in the dental model. In contrast to this, the antagonist can have a very low height compared to the part of the dental model where a die is present, if there is no preparation die teeth in the antagonist.

Articulator Type/Brand

In some embodiments the virtual dental articulator is provided by selection from a number of different dental articulator brands or types, and the selected dental articulator comprises a virtual version and a physical version.

It is an advantage that different articulator types or brands can be used, because the different articulator types may comprise different dimensions, different sizes, different heights between the arms in the articulator, different settings, different angles in the different joints etc. The different articulator types and brand may for example be KaVo articulators, SAM articulators, Denar articulators etc.

Gypsum

In some embodiments the attachment of the dental model in the articulator is designed such that no gypsum or plaster material is used for the attachment.

It is an advantage that the dental model, i.e. the upper part and the lower part of the dental model, can be attached in the articulator using no gypsum or similar attachment material, since this will provide that the use of gypsum can be eliminated, and the laboratory can be free of gypsum, it will not be a dirty job with gypsum all over the place when the dental model is attached in the articulator, etc.

Definition of Height of Model

In some embodiments the height of the upper part and/or lower part of the dental model is defined as the maximum distance between the insical edge and/or occlusal edge of the teeth in the upper part and/or lower part of the dental model, respectively, and the part of the base of the upper part and/or lower part of the dental model, respectively, which is most far away from the incisal edge and/or occlusal edge of the teeth in the upper part and/or lower part of the dental model, respectively.

In some embodiments the height of the dental model is the height of the lower part plus the height of the upper part of the dental model.

In some embodiments the height of the dental model is the height of the lower part plus the height of the upper part of the dental model, when the upper part and the lower part are arranged in static occlusion.

In some embodiments the height of the dental model is determined with the upper part and the lower part arranged in static occlusion.

Thus the height of the dental model may be less than the height of the upper part plus the height of the lower part, if the shapes of the teeth in the two parts have corresponding cusps and sulcuses such that the upper part and the lower part can be positioned in each others projections and grooves, or if the patient has an underhung jaw, has overbite and/or has protruding front teeth.

Spacer Elements

In some embodiments the spacer elements comprises one or more plates, one or more vertical pins, one or more triangular shaped blocks, one or more blocks with an inclination side, and/or one or more tripods with individually adjustable height of each the three legs of the tripod.

In some embodiments a spacer element is adapted to be mounted as a lower spacer element and/or as an upper spacer element.

The lower spacer element may be used to attach the lower part of the dental model to the lower arm of the articulator.

The upper spacer element may be used to attach the upper part of the dental model to the upper arm of the articulator.

In some embodiments the spacer elements are standard spacer elements from a manufacturer of spacer elements.

In some embodiments one or more of the spacer elements is defined as a base element.

The base element may be an element connecting the spacer element(s) with the arms of the articulator.

In some embodiments the one or more spacer elements are adapted to be reusable.

In some embodiments one or more of the spacer elements are adapted to be manufactured for the specific dental model.

In this way a spacer element with an inclined side may be manufactured for the dental model, if for example the dental model is intended to be arranged in the articulator with an angle relative to the horizontal plane. By manufacturing a spacer element for the specific dental model case, it may be easy to obtain the correct angle of the dental model in the articulator. The spacer element may then be manufactured in a cheaper material than the dental model or may be manufactured by a faster and/or cheaper manufacturing method than the dental model.

Manufacturing of Spacer Elements and/or Dental Model

In some embodiments the one or more spacer elements and the dental model are adapted to be manufactured separately.

Thus if one or more of the spacer elements are adapted to be manufactured for the attachment of the specific dental model, then the spacer element(s) and the dental model may be manufactured separately, for example using different manufacturing materials, and manufacturing time may be saved.

In some embodiments the one or more spacer elements and the dental model are adapted to be manufactured jointly.

Thus if one or more of the spacer elements are adapted to be manufactured for the attachment of the specific dental model, then the spacer element(s) and the dental model may be manufactured jointly, for example if the spacer element(s) and the dental model are manufactured in the same material, then the spacer element(s) and the upper part and/or lower part of the dental model may be manufactured as one piece, or manufactured as two or more pieces, also for example if the materials of the dental model and the spacer elements(s) are not the same. The spacer element(s) and the dental model may be manufactured jointly in different materials, if the manufacturing machine provides the possibility of doing this.

In some embodiments the manufactured dental model is adapted to be manufactured by means of direct digital manufacturing.

Direct digital manufacturing may be termed computer controlled manufacturing, rapid prototyping manufacturing, computer aided manufacturing (CAM) etc. CAM may be a numerical control (NC) programming tool, wherein two-dimensional (2-D) or three-dimensional (3-D) models of components, the dental model and maybe spacer elements, generated in the CAD software performing the method according to the invention, are used to generate G-code to drive computer numerically controlled CNC machine tools, such as for 3D printing, 3D milling etc.

In some embodiments the direct digital manufacturing is by additive fabrication.

In some embodiments the direct digital manufacturing is by subtractive fabrication.

In some embodiments the dental model is adapted to be manufactured by means of 3D printing.

3D printing is an example of additive manufacturing.

In some embodiments the dental model is adapted to be manufactured by means of milling.

In some embodiments the dental model is adapted to be manufactured by means of laser sintering.

Milling and laser sintering are examples of subtractive fabrication.

Library

In some embodiments one or more of the virtual spacer elements are adapted to be selected from a digital library of spacer elements in different shapes, forms and sizes.

Positioning of Model in Articulator

In some embodiments the orientation of the 3D virtual dental model in the dental articulator is provided from a facebow measurement and/or from an x-ray scan and/or from a CT scan of the patient and/or from a mid-value measurement or estimate.

It is an advantage that if the orientation of the 3D virtual model should be precise and accurate and reproduce the patient's actual anatomy and physiology, then a facebow measurement of the patient's face and jaw movements and bite and occlusion parameters may be performed. The parameters of the patient may also be derived from an x-ray or CT scan.

Alternatively, if no facebow data or x-ray or CT data are available or if the orientation of the dental model should not be determined precisely, then a mid-value estimate may be used.

Dental Preparation

In some embodiments one or more teeth in the dental model have been prepared for attachment of a dental restoration, such as a crown or a bridge.

Typically a dental model is produced and tested in an articulator if a restoration is made on the patient's teeth, if an implant is made, if a denture is made, and/or if an orthodontic treatment is planned.

Designing Dental Restoration

In some embodiments the method comprises designing a dental restoration for a preparation in the dental model of the patient's set of teeth.

The restoration may be designed before the dental model is manufactured, such that the restoration is also manufactured as part of the manufacturing process. The dental model and the restoration may be manufactured separately or jointly.

In some embodiments the method comprises designing the restoration for the dental model in accordance with the occlusion of the dental model tested in the articulator.

In the articulator both dynamic and static occlusion of the patient's set of teeth may be tested.

Connecting Elements

In some embodiments the one or more spacer elements and/or the upper part and/or lower part of the dental model comprises one or more connecting elements for connecting the spacer elements together and/or for connecting the upper part of the dental model with a spacer element and/or for connecting the lower part of the dental model with a spacer element.

In some embodiments the connecting elements are shaped as protrusions and holes, such that a protrusion in a first spacer element and/or in the upper part and/or lower part of the dental model connects with an opposite hole in a second spacer element and/or in the lower part and/or upper part of the dental model, respectively.

Connecting elements in the form of for example protrusions and holes may also be used to attach spacer elements to the upper arm and lower arm of the articulator. Connecting elements in the spacer elements, in the upper part and/or lower part of the dental model and/or in the upper arm or lower arm of the articulator may have any structure or function suitable for connecting components together.

Alternatively and/or additionally, the connection of the dental model with the spacer elements and/or the connection of a spacer element with other spacer elements and/or the connection of the upper arm and/or lower arm of the articulator with spacer elements can be performed by means of glue, tape, other kinds of sticking materials, by using a plastic material for at least parts of the spacer elements and/or of the dental model and/or the upper arm or lower arm of the articulator, where the plastic material becomes adhesive when melting it etc.

In some embodiments the upper and lower spacer elements are adapted to be attached to gypsum for attaching the dental model in the articulator using said gypsum.

Gypsum may then be used to attach the lower spacer element to the lower arm of the articulator and/or to attach the lower spacer element to the lower part of the dental model. Likewise, gypsum may be used to attach the upper spacer element to the upper arm of the articulator and/or to attach the upper spacer element to the upper part of the dental model.

Scanning Means

In some embodiments the 3D scanning is intra oral scanning of at least part of the patient's set of teeth, and/or scanning of at least part of an impression of the patient's set of teeth, and/or scanning of at least part of a model of the patient's set of teeth.

In some embodiments the 3D scanning is performed by means of laser light scanning, white light scanning, probe-scanning, X-ray scanning, and/or CT scanning.

The present invention relates to different aspects including the method described above and in the following, and corresponding methods, devices, kits, apparatuses, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system for virtually designing the attachment of a manufactured dental model of a patient's set of teeth in a physical dental articulator by means of one or more kinds of spacer elements, where the system comprises:
  means for obtaining a virtual 3D dental model of the patient's set of teeth, where the virtual 3D dental model is provided by means of 3D scanning;
  means for providing a virtual dental articulator type corresponding to a physical dental articulator, where the dental articulator comprises an upper arm and a lower arm and has a known articulator height, which is the distance between the upper arm and the lower arm in the static position of the dental articulator;
  means for providing a minimum height of the dental model, where the height of the dental model is the height of an upper part and the height of a lower part of the dental model;
  means for providing one or more kinds of virtual spacer elements with predetermined heights, where each kind of virtual spacer element corresponds to a physical spacer element;
  means for determining a manufacture height of the dental model and means for determining the number of each of the kinds of spacer elements to be used for the attachment of the manufactured dental model in the physical articulator, such that the manufacture height of the dental model and the total effective spacer element height, which is the added height of the determined spacer elements, equal the articulator height, and where the manufacture height of the dental model is not less than the minimum height of the dental model.

Disclosed is a system comprising a nontransitory computer readable medium having one or more computer instructions stored thereon, where said computer instructions comprises instructions for carrying out a method for virtually designing the attachment of a manufactured dental model of a patient's set of teeth in a physical dental articulator by means of one or more kinds of spacer elements, where the method comprises:
  obtaining a virtual 3D dental model of the patient's set of teeth, where the virtual 3D dental model is provided by means of 3D scanning;
  providing a virtual dental articulator type corresponding to a physical dental articulator, where the dental articulator has a known articulator height, which is the distance between the upper arm and the lower arm of the articulator in the static position;
  providing a minimum height of the dental model, where the height of the dental model is the height of an upper part and the height of a lower part of the dental model;
  providing one or more kinds of virtual spacer elements with predetermined heights, where each kind of virtual spacer element corresponds to a physical spacer element;
  determining a manufacture height of the dental model and determining the number of each of the kinds of spacer elements to be used for the attachment of the manufactured dental model in the physical articulator, such that the manufacture height of the dental model and the total effective spacer element height, which is the added height of the determined spacer elements, equal the articulator height, and where the manufacture height of the dental model is not less than the minimum height of the dental model.

Furthermore, in particular, disclosed herein is a kit for the attachment of a manufactured dental model of a patient's set of teeth in a physical dental articulator by means of s one or more kinds of pacer elements, where the kit comprises:
  a computer system comprising:
    means for obtaining/displaying/comprising a virtual 3D dental model of the patient's set of teeth, where the virtual 3D dental model is provided by means of 3D scanning;
    means for providing/displaying/comprising a virtual dental articulator type having a corresponding physical dental articulator, where the dental articulator comprises an upper arm and a lower arm and has a known articulator height, which is the distance between the upper arm and the lower arm in the static position of the dental articulator;
    means for providing/comprising a minimum height of the dental model, where the height of the dental model is the height of an upper part and the height of a lower part of the dental model;
    means for providing/displaying/comprising one or more kinds of virtual spacer elements with predetermined heights, where each kind of virtual spacer element has a corresponding physical spacer element;

means for determining a manufacture height of the dental model and determining the number of each of the kinds of spacer elements to be used for the attachment of the manufactured dental model in the physical articulator, such that the manufacture height of the dental model and the total effective spacer element height, which is the added height of the determined spacer elements, equal the articulator height, and where the manufacture height of the dental model is not less than the minimum height of the dental model.

one or more kinds of physical spacer elements with predetermined heights corresponding to the one or more virtual spacer elements.

Furthermore, the kit may further comprise a physical dental articulator corresponding to the virtual dental articulator.

Furthermore, the invention relates to a computer program product comprising program code means for causing a data processing system to perform the method according to any of the embodiments, when said program code means are executed on the data processing system, and a computer program product, comprising a computer-readable medium having stored there on the program code means.

According to an aspect of the invention, disclosed is a method of virtually planning/designing/arranging the attachment of a manufactured dental model of a patient's set of teeth in a physical dental articulator, where the method comprises:

obtaining a virtual 3D dental model of the patient's set of teeth, where the virtual 3D dental model is provided by means of 3D scanning;

providing a virtual dental articulator type or brand having a corresponding physical dental articulator, where the dental articulator comprises an upper arm and a lower arm and has a known distance between the upper arm and the lower arm in the static position of the dental articulator;

setting or providing the orientation of the 3D virtual dental model in the virtual articulator corresponding to the orientation which the manufactured dental model is intended to be arranged with in the physical dental articulator;

providing an initial height of the 3D virtual dental model;

calculating an initial total effective spacer elements height, where the total effective height of the spacer elements is the added height of all the spacer elements used for attaching the dental model in the articulator;

such that the height of the dental model and the total effective height of the spacer elements equal the height/distance between the upper arm and the lower arm of the dental articulator, whereby the manufactured dental model is adapted to be attached between the upper arm and the lower arm in the physical articulator by means of the one or more kinds of spacer elements;

providing one or more kinds of virtual spacer elements with predetermined heights, where each kind of virtual spacer element has a corresponding physical spacer element;

determining if any combination and/or number of the different kinds of spacer elements provides the initial total effective spacer element height;

if no combination and/or number of the different kinds of spacer elements provides the initial total effective spacer element height, then:

calculate an adjusted total effective spacer elements height, which is possible to obtain using the spacer elements; and calculate an adjusted dental model height, such that the adjusted dental model height and the adjusted total effective spacer element height equal the distance between the upper arm and the lower arm of the dental articulator.

According to an aspect of the invention, disclosed is a method of virtually planning/designing/arranging the attachment of a manufactured dental model of a patient's set of teeth in a physical dental articulator, where the method comprises:

obtaining a virtual 3D dental model of the patient's set of teeth, where the virtual 3D dental model is provided by means of 3D scanning;

providing a virtual dental articulator type or brand having a corresponding physical dental articulator, where the dental articulator comprises an upper arm and a lower arm and has a known distance between the upper arm and the lower arm in the static position of the dental articulator;

setting or providing the orientation of the 3D virtual dental model in the virtual articulator corresponding to the orientation which the manufactured dental model is intended to be arranged with in the physical dental articulator;

providing one or more kinds of virtual spacer elements, where each kind of virtual spacer element has a corresponding physical spacer element;

providing an adjustable height of the dental model, where the height of the dental model is the height of a lower part and an upper part of the dental model;

providing an adjustable total effective height of the spacer elements; where the total effective height of the spacer elements is the added height of all the spacer elements when arranged for attaching the dental model in the articulator;

determining the height of the dental model to be manufactured; and determining the number of each kind of spacer elements to be used when attaching the dental model in the physical articulator, whereby the manufactured dental model is adapted to be attached between the upper arm and the lower arm in the physical articulator by means of the one or more kinds of spacer elements, such that the height of the dental model and the total effective height of the spacer elements equal the height/distance between the upper arm and the lower arm of the dental articulator.

According to an aspect of the invention, disclosed is a method for mounting a physical teeth model in articulator without using gypsum, where the method is suitable for mounting teeth models, upper and lower, where the occlusion plane is adapted to have any angle relative to the horizontal plane in the dental articulator, such that the model is adapted to be arranged with an angle relative to the horizontal plane, where in:

the teeth models are printed with a base such that the model and the base can be directly inserted in articulator without using gypsum; or at least one of the teeth models is printed and a base and/or interface block is printed separately, the teeth models and the base and/or interface block are then attached together and arranged in articulator without using gypsum; or at least one of the teeth models is printed and one or more standard plates/blocks are used in a suitable combination for arranging the teeth models correct in the articulator.

According to an aspect of the invention, disclosed is a method for virtually modeling the attachment of a physical model of a set of teeth in an articulator, comprising:
obtaining a virtual 3D model of the set of teeth based on a virtual 3D representation of the set of teeth;
virtually modeling attachment means for the attachment of the physical model of the set of teeth to a physical articulator;
wherein the attachment means are modeled such that the physical model of the set of teeth can be attached to the physical articulator without using gypsum.

Disclosed is a method of virtually planning/designing/arranging the attachment of a manufactured dental model of a patient's set of teeth in a physical dental articulator, where the manufactured dental model is adapted to be attached between an upper arm and a lower arm in the physical articulator by means of the one or more kinds of spacer elements, where the method comprises:
obtaining a virtual 3D dental model of the patient's set of teeth, where the virtual 3D dental model is provided by means of 3D scanning;
providing a virtual dental articulator type having a corresponding physical dental articulator, where the dental articulator comprises an upper arm and a lower arm and has a known distance between the upper arm and the lower arm in the static position of the dental articulator;
setting or providing the orientation of the 3D virtual dental model in the virtual articulator corresponding to the orientation which the manufactured dental model is intended to be arranged with in the physical dental articulator;
providing one or more kinds of virtual spacer elements, where each kind of virtual spacer element has a corresponding physical spacer element for use when attaching the dental model in the physical articulator;
determining a total effective height of the spacer elements and a corresponding height of the dental model to be manufactured, where the determined height of the dental model and the determined total effective height of the spacer elements together equal the distance between the upper arm and the lower arm of the dental articulator in said static position, and
determining the number of each kind of spacer elements required to obtain the total effective height of the spacer elements
where the total effective height of the spacer elements is the added height of all the spacer elements when arranged for attaching the dental model in the articulator, and where the height of the dental model is the height of a lower part and an upper part of the dental model.

In one embodiment, the step of determining the total effective height of the spacer elements and a corresponding height of the dental model to be manufactured and the step of determining the number of each kind of spacer elements required to obtain the total effective height of the spacer elements is performed as one step in which the total effective height of the spacer elements the number of each kind of spacer elements required to obtain the total effective height are determined simultaneously.

Disclosed is a method of virtually designing the attachment of a manufactured dental model of a patient's set of teeth in a physical dental articulator by means of spacer elements, where the method comprises:
providing a virtual 3D dental model of the patient's set of teeth, where the virtual 3D dental model is obtained by means of 3D scanning;
providing a virtual dental articulator type corresponding to a physical dental articulator, where the dental articulator has a known articulator height, which is the distance between the upper arm and the lower arm of the articulator in the static position;
providing a minimum height of the dental model, where the height of the dental model is the height of the upper part and the height of the lower part of the dental model;
providing one or more kinds of virtual spacer elements with predetermined heights, where each kind of virtual spacer element corresponds to a physical spacer element;
determining a manufacture height of the dental model and determining the number of each of the kinds of spacer elements to be used for the attachment of the manufactured dental model in the physical articulator,
such that the manufacture height of the dental model and the total effective spacer element height, which is the added/collected height of the determined spacer elements, equal the articulator height, and where the manufacture height of the dental model is not less than the minimum height of the dental model.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIG. 16 shows a flowchart of obtaining information for arranging a dental model in a virtual articulator.

DETAILED DESCRIPTION

In the following description, reference is made to the accompanying figures, which show by way of illustration how the invention may be practiced.

Figure 1:
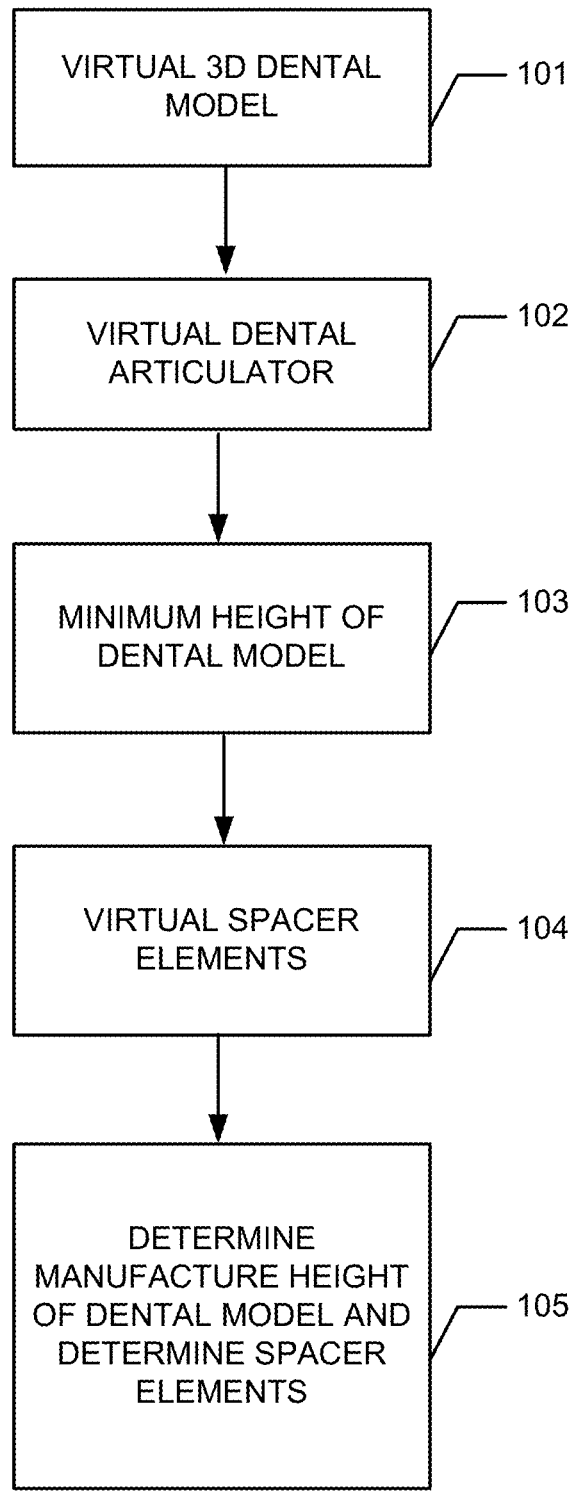
FIG. 1 shows an example of a flowchart of a method for virtually designing the attachment of a manufactured dental model of a patient's set of teeth in a physical dental articulator by means of one or more kinds of spacer elements.

FIG. 1 shows an example of a flowchart of a method for virtually designing the attachment of a manufactured dental model of a patient's set of teeth in a physical dental articulator by means of one or more kinds of spacer elements.

In step 101 a virtual 3D dental model of the patient's set of teeth is obtained, where the virtual 3D dental model is provided by means of 3D scanning.

In step 102 a virtual dental articulator type corresponding to a physical dental articulator is provided, where the dental articulator comprises an upper arm and a lower arm and has a known articulator height, which is the distance between the upper arm and the lower arm in the static position of the dental articulator.

In step 103 a minimum height of the dental model is provided, where the height of the dental model is the height of an upper part and the height of a lower part of the dental model.

In step 104 one or more kinds of virtual spacer elements with predetermined heights is provided, where each kind of virtual spacer element corresponds to a physical spacer element.

In step 105 a manufacture height of the dental model is determined and the number of each of the kinds of spacer elements to be used for the attachment of the manufactured dental model in the physical articulator is determined, such that the manufacture height of the dental model and the total effective spacer element height, which is the added height of the determined spacer elements, equal the articulator height, and where the manufacture height of the dental model is not less than the minimum height of the dental model.

Figure 2:
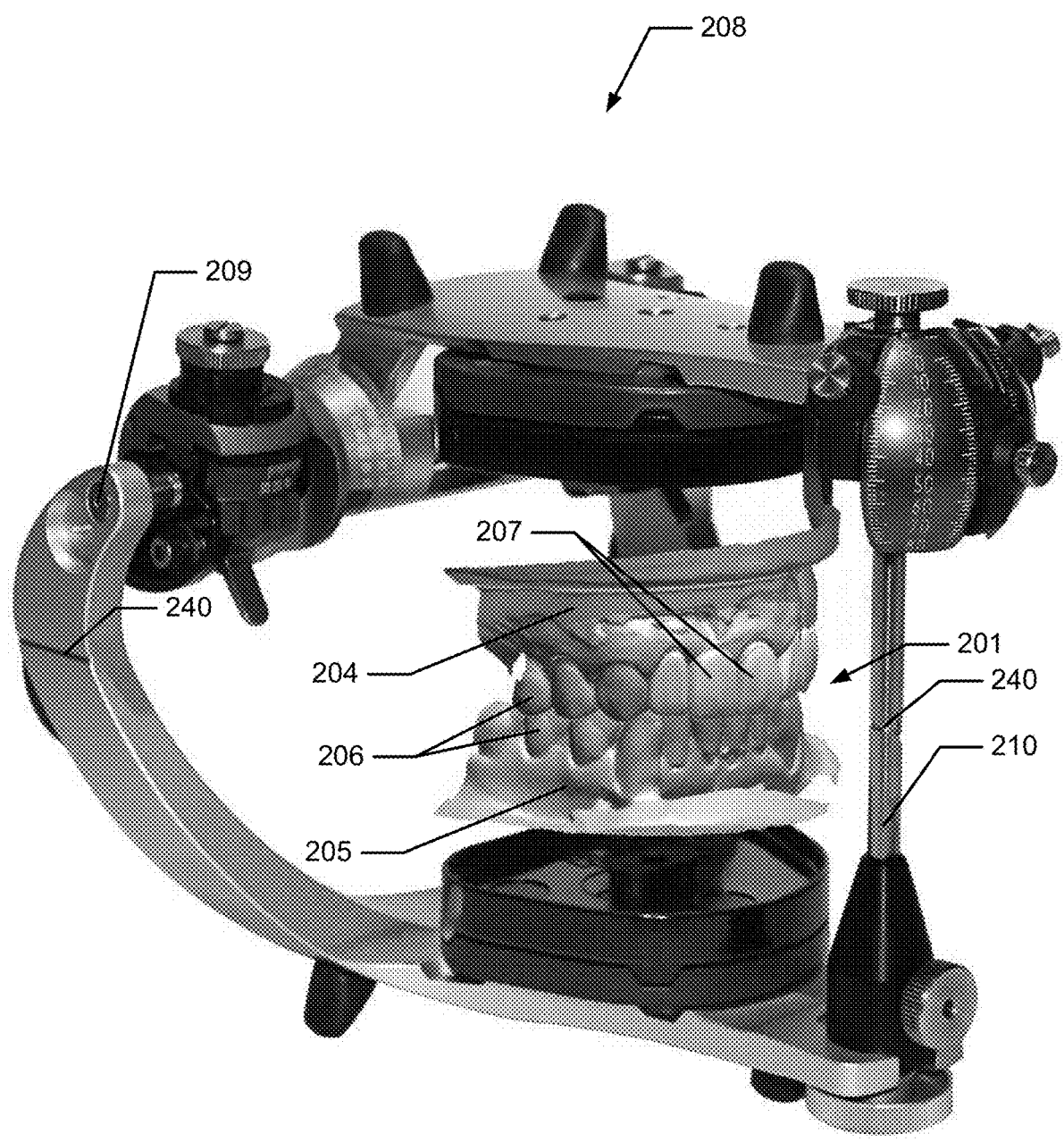
FIG. 2 shows an example of a virtual articulator and a virtual dental model.

FIG. 2 shows an example of a virtual articulator and a virtual dental model.

FIG. 2 shows a virtual articulator 208 with a virtual 3D dental model 201 comprising a virtual upper jaw 204 with teeth 206 and a virtual lower jaw 205 with teeth 206. Some of the teeth 207 in the upper jaw 204 have been or are being restored, and the virtual articulator 208 is used to simulate the movements of the jaws 204, 205 e.g. simulating the static occlusion and/or the dynamic occlusion to test if the restored teeth 207 fit into the rest of teeth of a patient.

The virtual articulator 208 comprises setting opportunities 209, 210 for controlling the movement of the jaws 204, 205 along an occlusial axis, a laterotrusial-mediotrusial axis, a protrusial-retrusial axis etc. The indentations 240 indicate where the dental technician will arrange a default occlusial plane in the form of a rubber band. The jaws 204, 205 moves up and down along the occlusial axis, and the jaws 204, 205 performs forward-sidewards movements to both left and right along the laterotrusial-mediotrusial axis. The jaws 204, 205 can also perform protrusion, which is direct forward movement, and retrusion, which is direct backward movement.

The different movement directions possible may be:
protrusion;
retrusion;
laterotrusion to the right;
laterotrusion to the left;
mediotrusion to the right;
mediotrusion to the left;
latero-re surtrusion to the right;
latero-re surtrusion to the left.

Figure 3:
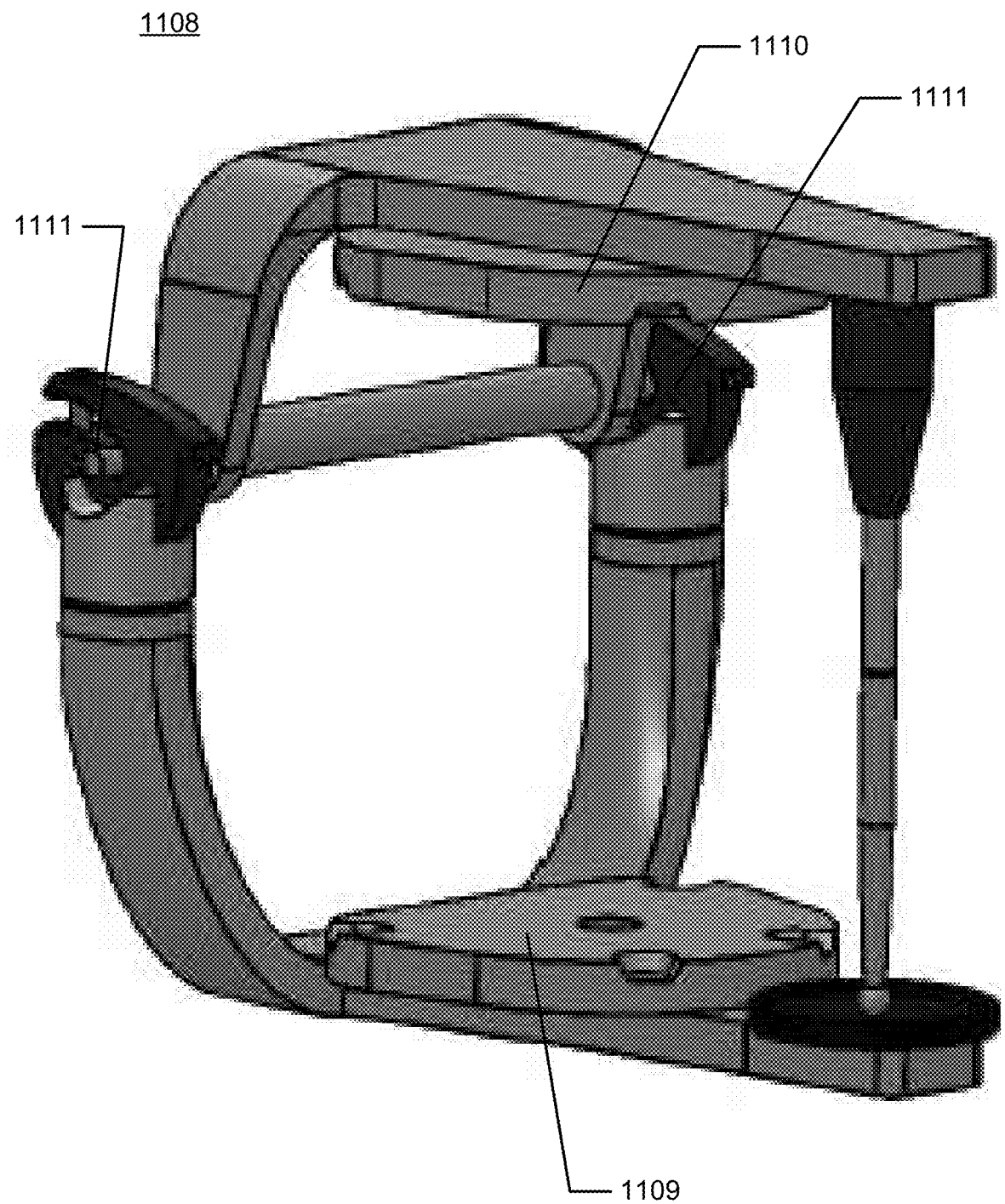
FIG. 3 shows an example of a virtual articulator.

FIG. 3 shows an example of a virtual articulator.

The virtual articulator 1108 is a virtual version of a physical, mechanical device used in dentistry to which casts of the upper and lower teeth are fixed and reproduces recorded positions of the lower teeth in relation to the upper teeth. An articulator can be adjustable in one or more of the following areas: condylar angle, Bennett side-shift, incisal and cuspid guidance, and shape of the glenoid fossae and eminintiae. An articulator may reproduce normal lower movements during chewing. An articulator may be adjusted to accommodate the many movements and positions of the lower teeth in relation to the upper teeth as recorded in the mouth. Thus the virtual articulator may perform all the movements etc. as the mechanical articulator.

The virtual articulator 1108 comprises a bottom base 1109 onto which the virtual model of the lower teeth or lower jaw is adapted to be arranged, a top base 1110 onto which the virtual model of the upper teeth or upper jaw is adapted to be arranged. The different virtual joints, slides or setting means 1111 indicates the joints, slides and other settings of a mechanical articulator where the different areas mentioned above can be adjusted to the features of a specific patient.

FIG. 4 shows examples of virtual articulators resembling physical articulators form different manufacturers.

Figure 4A:
FIG. 4 shows examples of virtual articulators resembling physical articulators form different manufacturers.
Figure 4B:
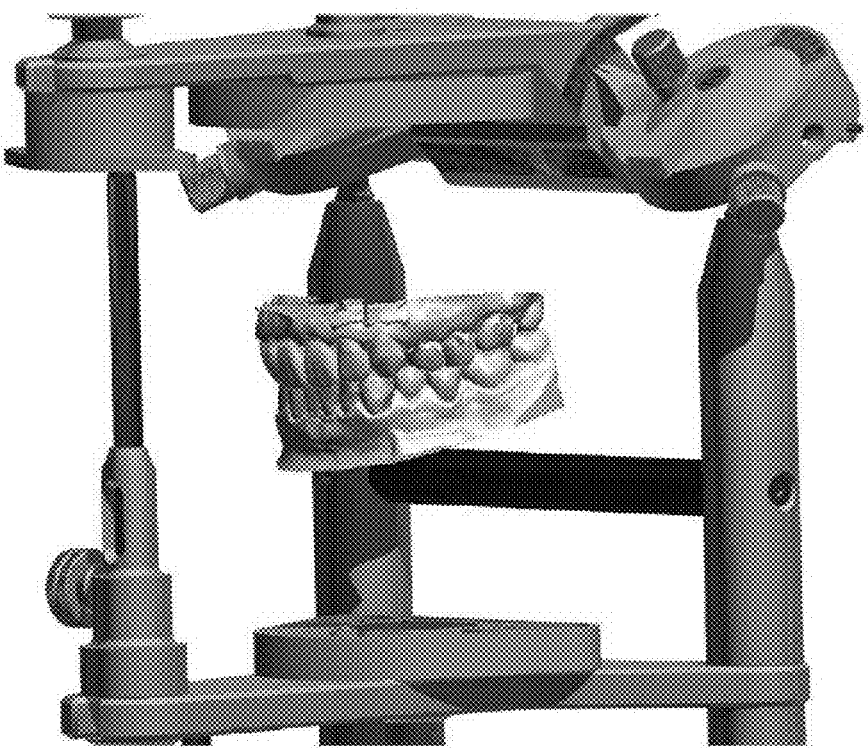
Figure 4C:
Figure 4D:
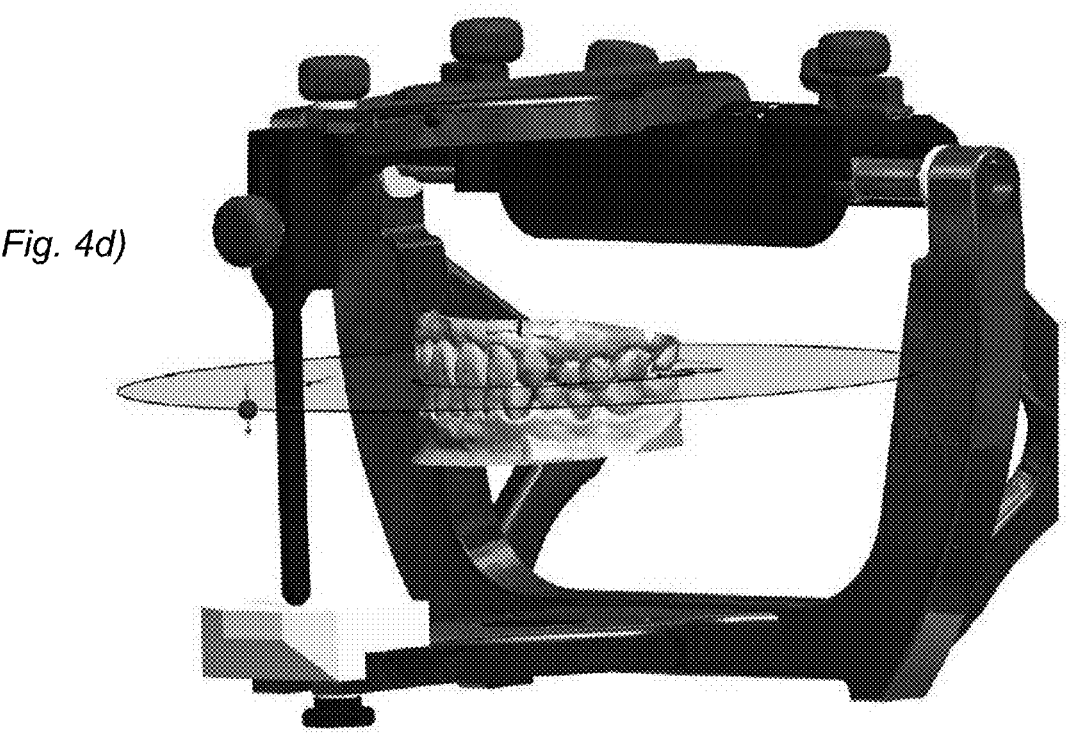

FIG. 4a) shows an articulator from KaVo.
FIG. 4b) shows an articulator from SAM.
FIG. 4c) shows an articulator from Denar.
FIG. 4d) shows the articulator from Denar with the occlusal plane arranged relative to the virtual teeth model.

FIG. 5 shows examples of setting or providing the angle of the occlusal plane of the virtual dental model relative to the horizontal plane in the virtual dental articulator.

The angle of the occlusion plane of the 3D virtual dental model 501 relative to the horizontal plane of the virtual dental articulator 508 corresponds to the angle relative to the horizontal plane which the manufactured dental model is intended to be arranged with in the physical dental articulator.

Figure 5A:
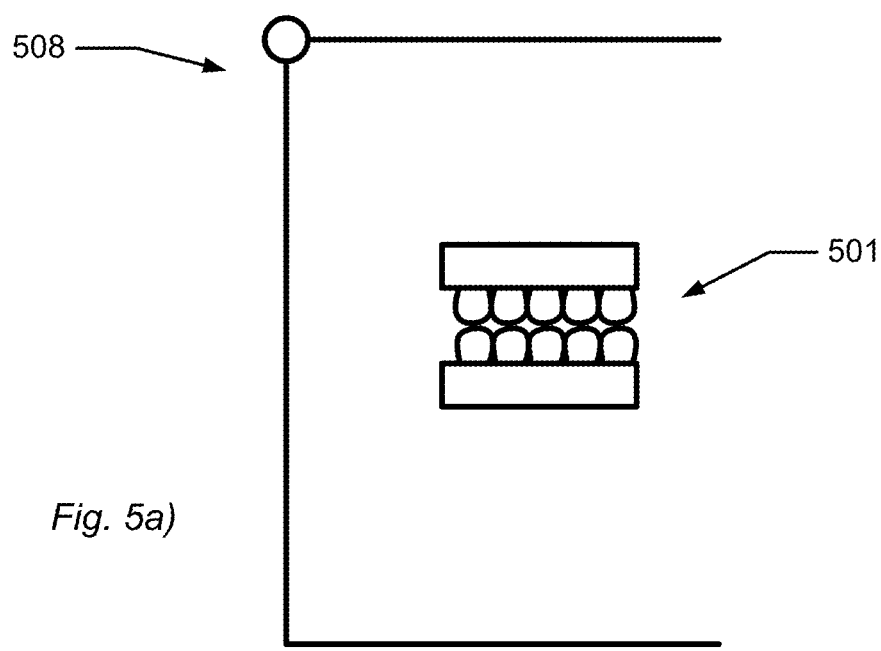
FIG. 5 shows examples of setting or providing the angle of the occlusal plane of the virtual dental model relative to the horizontal plane in the virtual dental articulator.

In FIG. 5a) the angle of the occlusal plane of the virtual dental model 501 relative to the horizontal plane of the articulator 508 is zero, since the occlusal plane of the virtual dental model corresponds to the horizontal plane of the articulator.

Figure 5B:
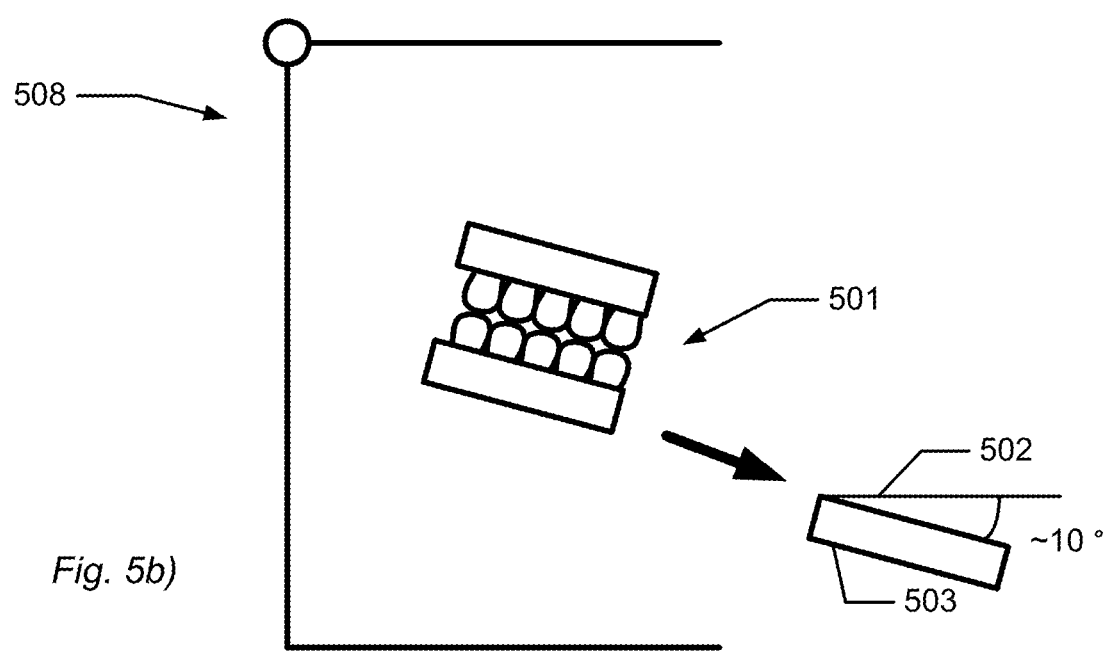

In FIG. 5b) the angle of the occlusion plane 503 of the virtual dental model is different than the horizontal plane 502 of the articulator, such as 10 degrees, as indicated in the extract in the lower right corner of the figure.

Figure 6:
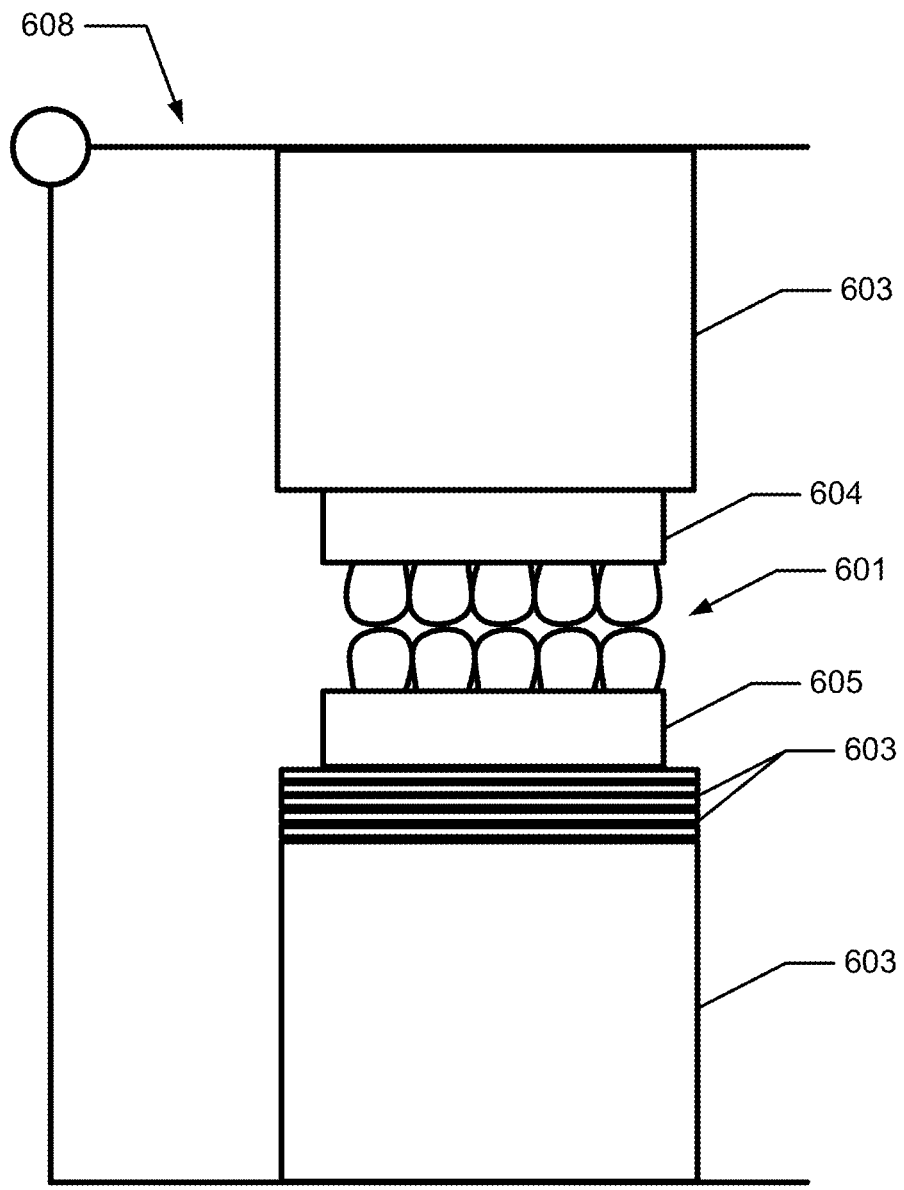
FIG. 6 shows an example of a dental model in an articulator using spacer elements.

FIG. 6 shows an example of attaching a dental model in an articulator using spacer elements.

The figure may represent both the virtual arrangement and the physical arrangement.

The dental model 601 comprising the upper teeth or jaw 604 and the lower teeth or jaw 605 is arranged in the articulator 608. The occlusal plane of the dental model corresponds to the horizontal plane of the articulator. The dental model 601 is attached in the articulator 608 by means of a number of spacer elements 603. The upper jaw 604 is attached by means of one larger spacer element 603 and the lower jaw 605 is attached by means of one larger spacer element and five smaller spacer elements 603.

FIG. 7 shows examples of the height of the dental model, the total height of the spacer elements and the distance or height between the upper and lower arm of the articulator.

Figure 7A:
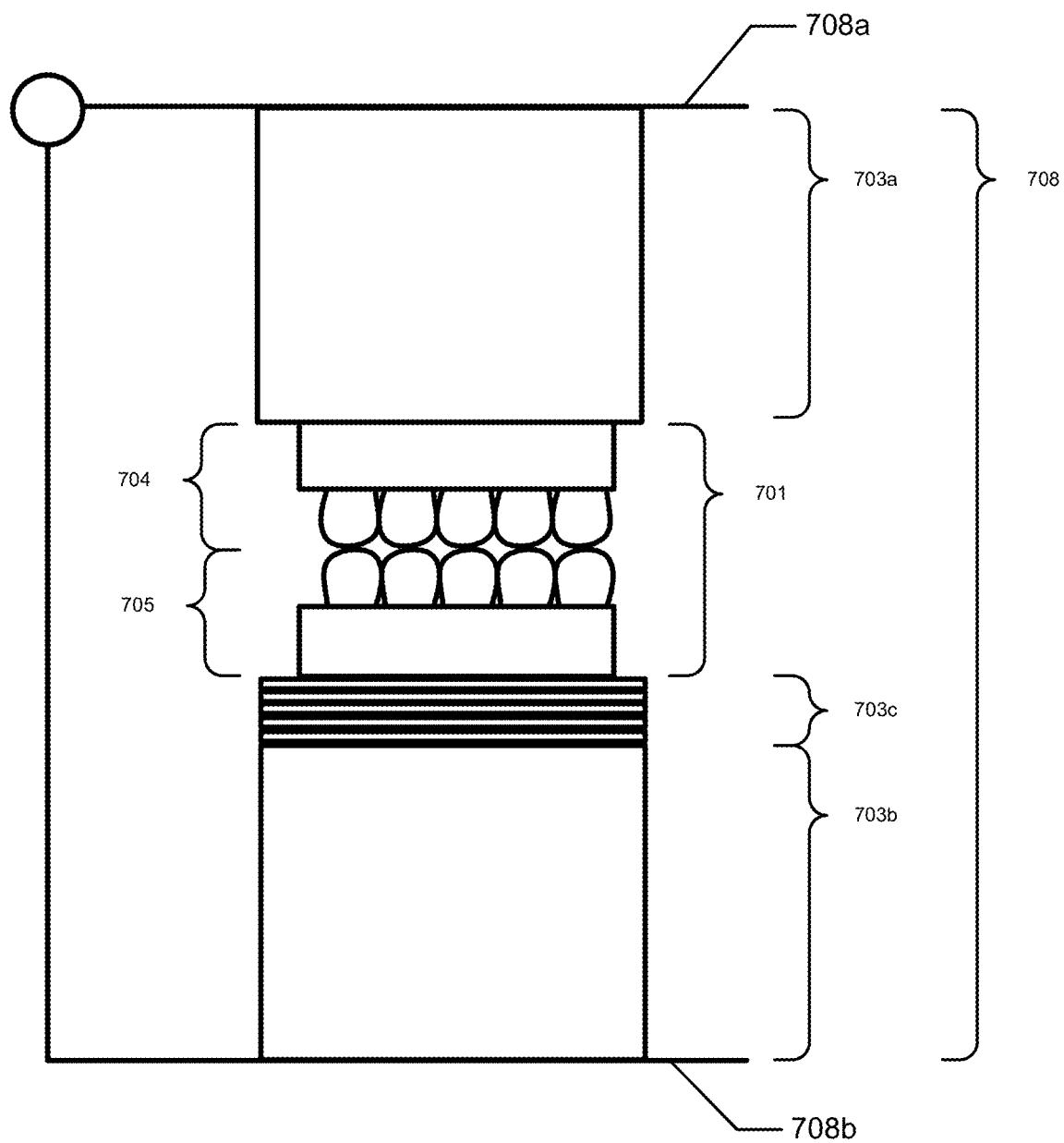
FIG. 7 shows examples of the height of the dental model, the total height of the spacer elements and the distance or height between the upper and lower arm of the articulator.

FIG. 7a) shows an example of an arrangement corresponding to FIG. 6, where the occlusal plane of the dental model corresponds to the horizontal plane of the articulator.

The height 701 of the dental model is the total height of the upper part 704 and the lower part 705 of the dental model.

The total effective height 703 of the spacer elements is the added height of each of the spacer elements 703a, 703b and 703c. The height 703c is the height of five smaller spacer elements, which each could be indicated by heights 703ci, 703cii, 703ciii, 703ciiii and 703civ.

The height 708 of the articulator is the distance between the upper arm 708a and the lower arm 708b of the articulator.

The height 701 of the dental model and the total effective height 703 of the spacer elements equal the height 708 of the articulator.

In this example no gypsum or other shapeable material is used for attaching the dental model in the articulator.

If gypsum is to be used, the gypsum is a part of the spacer elements, and the height of the gypsum would then be included in the total effective height of the spacer elements 703.

Figure 7B:
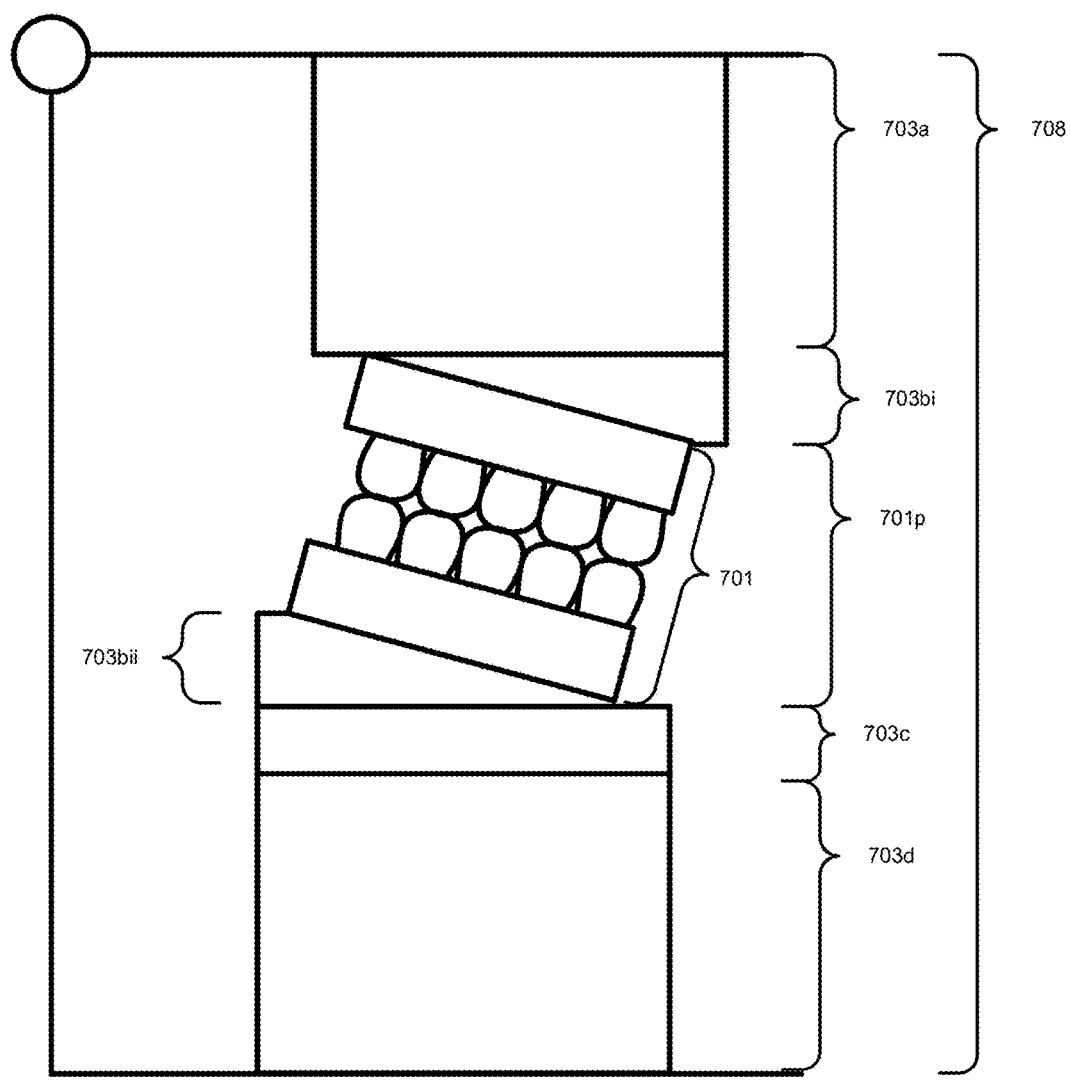

FIG. 7b) shows an example of an arrangement, where the occlusal plane of the dental model has an angle of for example 10 degrees relative to the horizontal plane of the articulator.

The height 701 of the dental model is the total height of the upper part and the lower part of the dental model.

The total effective height 703 of the spacer elements is the added height of each of the spacer elements 703a, 703bi, 703bii, 703c and 703d. Because the occlusal plane of the dental model has an angle relative to the horizontal plane of the articulator, at least some of the spacer elements may have an inclined side to match the angle of the occlusal plane relative to the horizontal plane. In this case the spacer elements 703bi and 703bii have inclined surfaces, and since the dental model is arranged with an inclination in the articulator, only the height of the spacer element 703bi is included in the total effective height of the spacer elements, and the height of the spacer element 703bii is not included in the total effective height. This can be confirmed by studying the figure.

The height 708 of the articulator is the distance between the upper arm 708a and the lower arm 708b of the articulator.

The projected height 701p of the dental model onto the vertical axis of the articulator and the total effective height 703 of the spacer elements equal the height 708 of the articulator.

FIG. 8 shows an example where the height of dental model is adjusted.

An object of the invention is to minimize the height of the dental model such that less material is used for manufacturing the dental model. There may be a predefined minimal possible height, which is a height that the dental model cannot be lower than since a preparation die tooth in the dental tooth may need to be a certain height for obtaining proper stability of the preparation die tooth in the model.

The antagonist, i.e. the opposite jaw of the jaw where a preparation die tooth is present, can be lower than the jaw with the preparation die tooth as the antagonist may just fit to the jaw with the preparation die tooth and the antagonist may not need to satisfy stability requirements.

The minimal height of the dental model may thus be determined by the minimal possible height, which is determined by stability requirements of the preparation die tooth, and by any predefined height of spacer elements. The height of the dental model must be exactly the difference between the articulator height and the total effective height of the spacer elements, so if the spacer elements have a predefined height, the height of the dental model may be adjusted to fit the total effective height of the spacer elements.

Figure 8A:
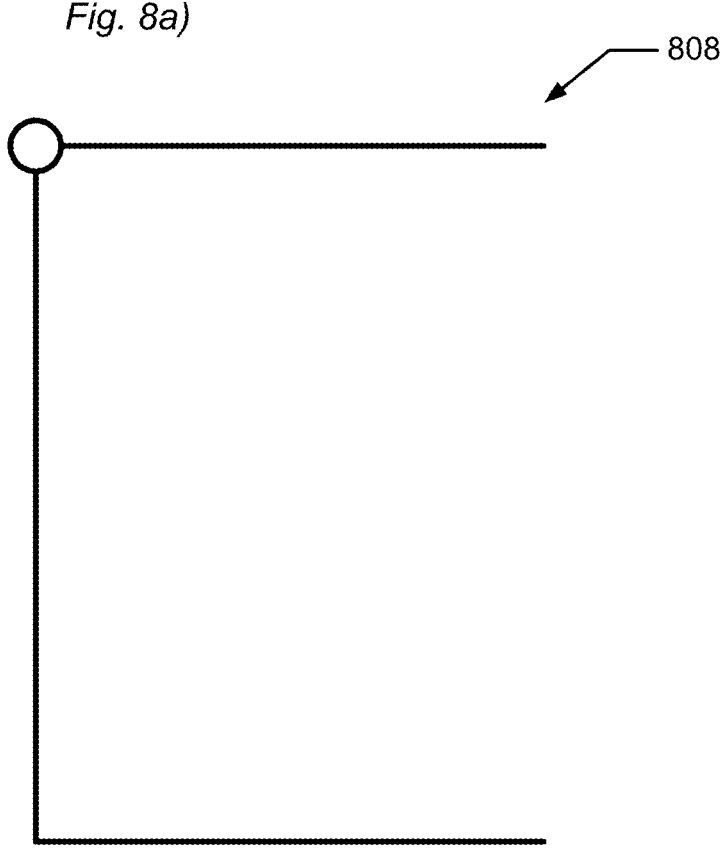
FIG. 8 shows an example where the height of dental model is adjusted.
Figure 8B:
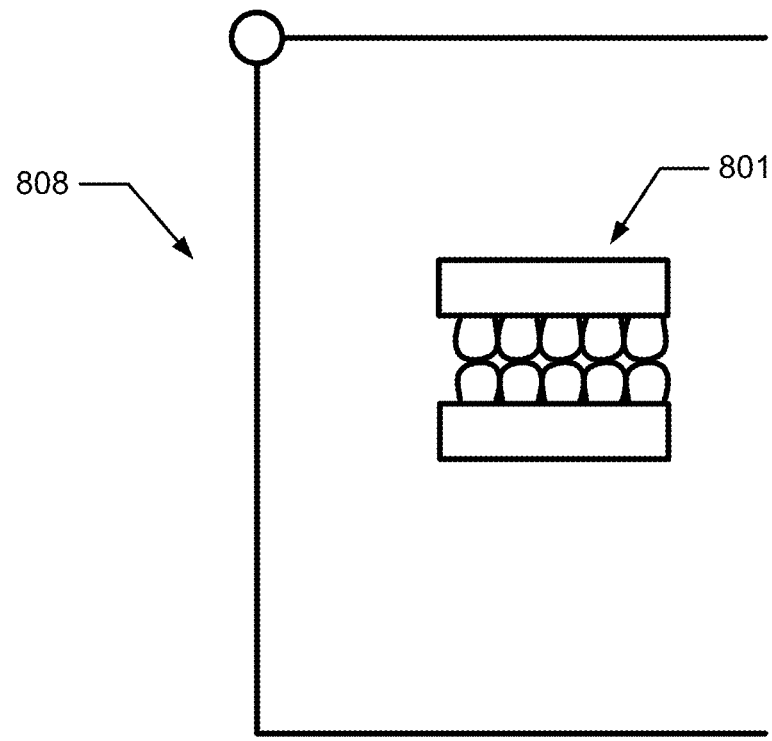
Figure 8C:
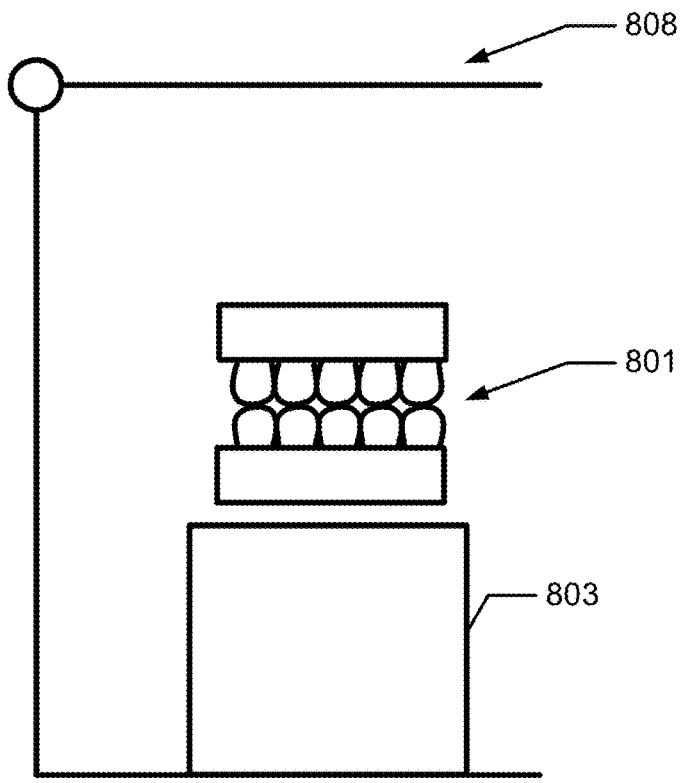
Figure 8D:
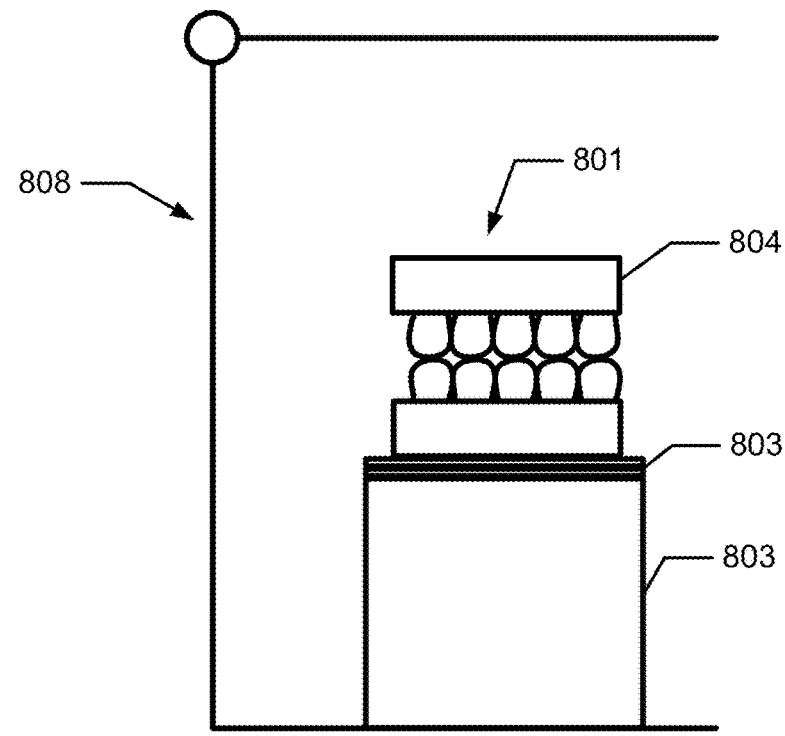
Figure 8E:
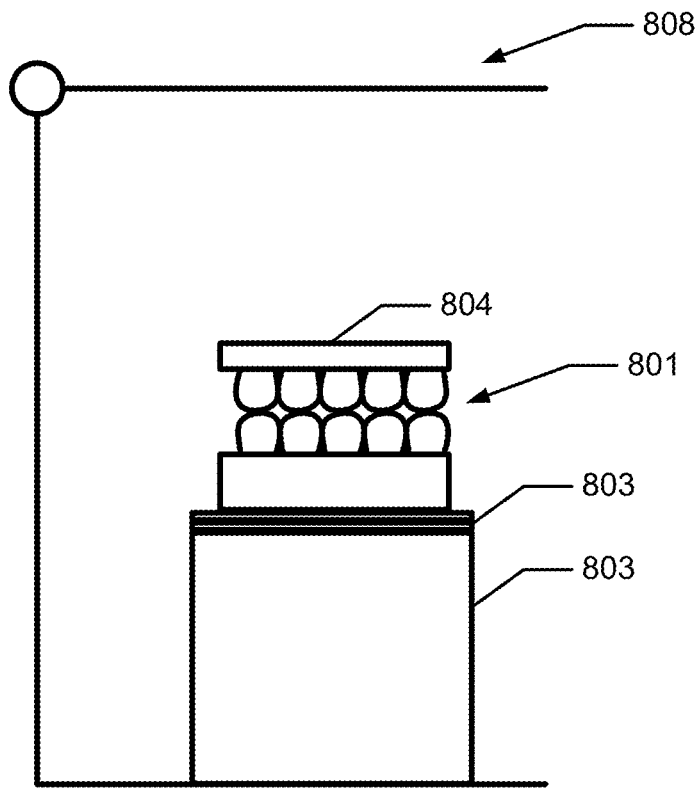
Figure 8F:
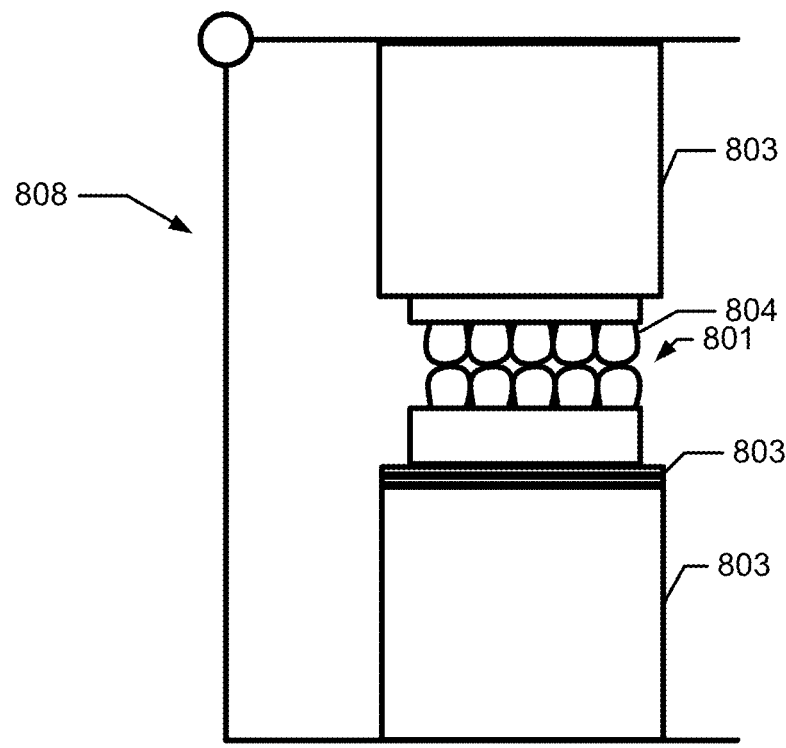

FIG. 8a)-FIG. 8f) shows how the virtual arrangement of the virtual dental model in the virtual articulator may be performed.

FIG. 8a) shows an example of the articulator 808.

FIG. 8b) shows an example where the dental model 801 is arranged virtually in the articulator 808. The angle of the occlusion plane of the dental model relative to the horizontal plane of the articulator may be predetermined, such as by a facebow measurement, or the angle be a standard angle etc. In this case the angle of the occlusion plane of the dental model relative to the horizontal plane of the articulator is zero, i.e. the occlusion plane corresponds to horizontal plane of the articulator.

FIG. 8c) shows an example where a spacer element 803 is virtually arranged in the articulator to 808 fix the dental model 801 in the articulator. The spacer element 803 is a high box shaped spacer element. However there is still a space between the dental model 801 and the spacer element 803, so more spacer elements may be required.

FIG. 8d) shows an example where more spacer elements 803 are virtually added such that the space between the dental model 801 and the box shaped spacer element is closed. The spacer elements 803 are in this case flat plates.

The upper part 804 of the dental model 801 has a standard height. The upper part 804 of the dental model 801 may on this case be the antagonist.

FIG. 8e) shows an example where the height of the upper part 804 of the dental model 801 is adjusted by being reduced. If the upper part 804 in this case is the antagonist, the required minimum height of the upper part 804 may be less than the height of the lower part 805 which may comprise the preparation die tooth. In this case it is the base part of the upper part that is reduced in height, i.e. the height of the teeth in the upper part 804 is not modified.

FIG. 8f) shows an example where a spacer element 803 is arranged between the upper arm of the articulator 808 and the upper part 804 of the dental model 801 for attaching the upper part 804 of the dental model 801 in the articulator 808. The spacer element 803 has a predefined height.

EXAMPLE 1

The height of the articulator (AH), i.e. the distance between the upper (UA) and lower arm (LA) of the articulator in static position is: AH=UA−LA=100 mm.

The dental model comprises a preparation die tooth of the type A in the upper part (UP) of the model, and a type A preparation requires that the minimum height of the upper part (UP) is UP=12 mm.

The type A preparation may for example be a preparation in an anterior tooth and the preparation die tooth may for example have straight side walls. A type B preparation may for example be a preparation in a molar tooth with tapered or inclined side walls etc.

The antagonist height may in this case have a minimum height of 8 mm. The antagonist is the lower part (LP) in this case, thus LP=8 mm.

This gives a total dental model (DM) height of DM=UP+LP=12 mm+8 mm=20 mm

This requires that the total effective height of the spacer elements (TESE) is:

$$AH-DM=TESE=100 \text{ mm}-20 \text{ mm}=80 \text{ mm}.$$

Both the upper part and the lower part of the dental model may be fixed to the articulator, i.e. the upper part should be attached to the upper articulator arm and the lower part should be attached to the lower articulator arm. Thus at least two spacer elements may be needed.

In this example there is no inclination of the dental model relative to the horizontal, and thus no spacer elements with an inclined side is required and there the total effective height of the spacer elements equals the actual height of the spacer elements.

In this example the different possible spacer elements to be used for attaching the dental model, have the following heights:

A: 70 mm
B: 40 mm
C: 20 mm
D: 10 mm
E: 5 mm
F: 2.5 mm
G: 1.25 mm

So in this case two spacer element B's could be used, since this would give 2*40 mm=80 mm which should be the total effective height of the spacer elements.

EXAMPLE 2

In this example the height of the articulator, i.e. the distance between the upper and lower arm is AH=110 mm The minimum height of the dental model is DM=18 mm, where the minimum height of the lower part with the preparation is LP=11 mm, e.g. a C type preparation, and the height of the antagonist, the upper part, is UP=7 mm.

The total effective height of the spacer elements should then be TESE=110 mm−18 mm=92 mm.

If two B spacer elements, 2*40 mm=80 mm, and two E spacer elements, 2*5 mm=10 mm, or one A spacer element, 80 mm, and one D spacer element, 10 mm, are used, then the total effective spacer element height is 80 mm+10 mm=90 mm. Thus 2 mm is missing in the total effective spacer element height. If spacer element F is used, which is 2.5 mm, then the total effective spacer element height would be 90 mm+2.5 mm=92.5 mm, which is 0.5 mm too much. Since the dental model cannot be made any smaller, it is not possible to compensate for an extra 0.5 mm. Thus the spacer element G which is 1.25 mm can be used, so the total effective height of the spacer elements becomes 90 mm+1.25 mm=91.25 mm. Thus 92 mm−91.25 mm gives 0.75 mm lacking in height, and these 0.75 mm in height may then be added to the dental model, which may then be manufactured to be 0.75 higher than the minimum possible height.

So the result is a total effective height of the spacer elements of:

TESE=91.25 mm.

And a dental model height of DM=18+0.75 mm=18.75 mm, where the extra 0.75 mm can be added to the upper part and/or the lower part of the dental model.

Then the total effective height of the spacer elements plus the height of the dental model equals the height of the articulator AH:

$$TESE+DM=91.25 \text{ mm}+18.75 \text{ mm}=110 \text{ mm}=AH.$$

In other examples the spacer elements may have other heights, and/or the height of the articulator in static position may be different, and/or the minimum possible heights of the dental model, both the minimum possible height of the jaw with the preparation die tooth and the minimum possible height of the antagonist may be different.

FIG. 9 shows examples of arrangements of dental models, where the dental models are arranged with an angle of the occlusal plane relative to the horizontal plane of the dental articulator.

Figure 9A:
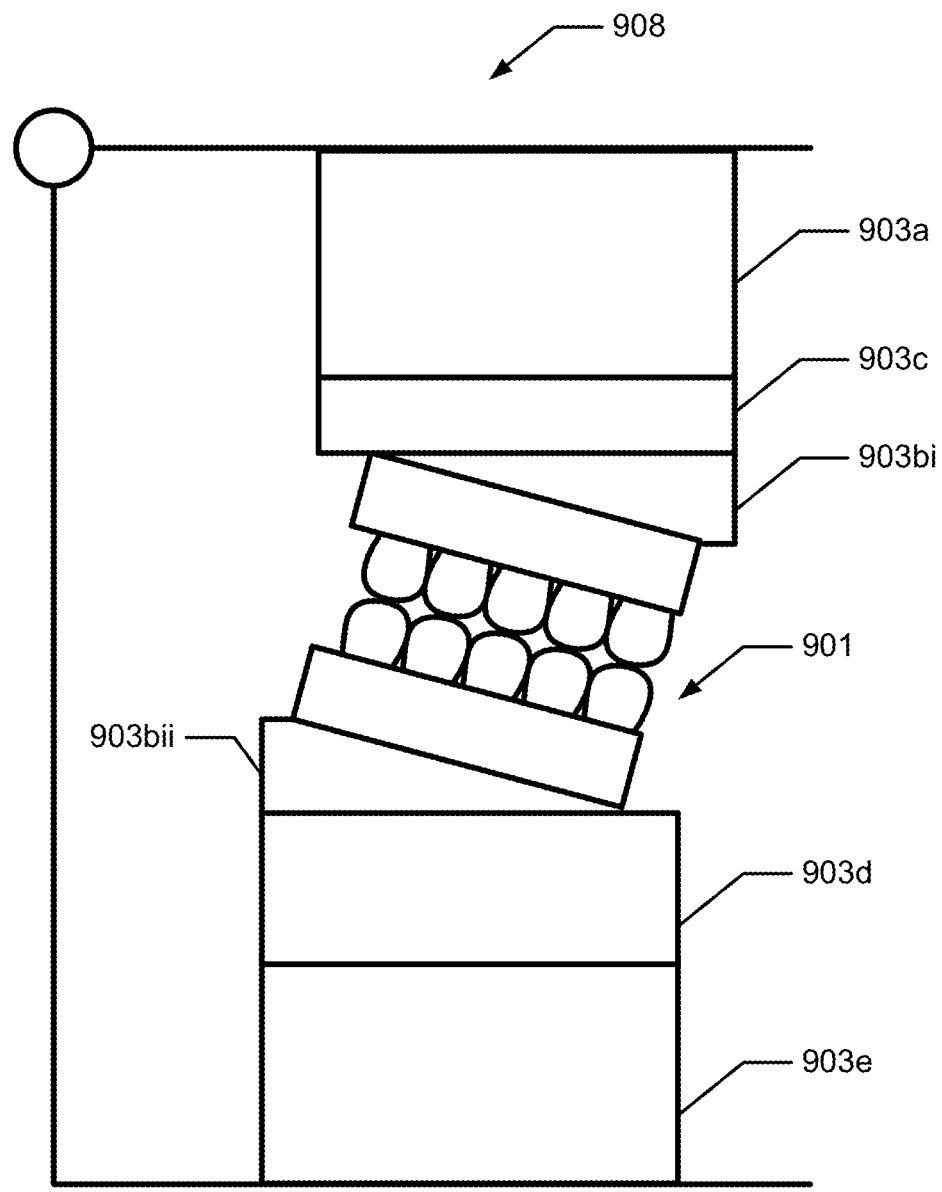
FIG. 9 shows examples of arrangements of dental models, where the dental models are arranged with an angle of the occlusal plane relative to the horizontal plane.

FIG. 9a) shows an example where a dental model 901 is arranged in the articulator 908 by means of a combination of six spacer elements 903, where two of the spacer elements 903bi and 903bii comprises inclined sides for retaining the inclined dental model 901, and where four of the spacer elements 903a, 903c, 903d and 903e are rectangular shaped.

Figure 9B:
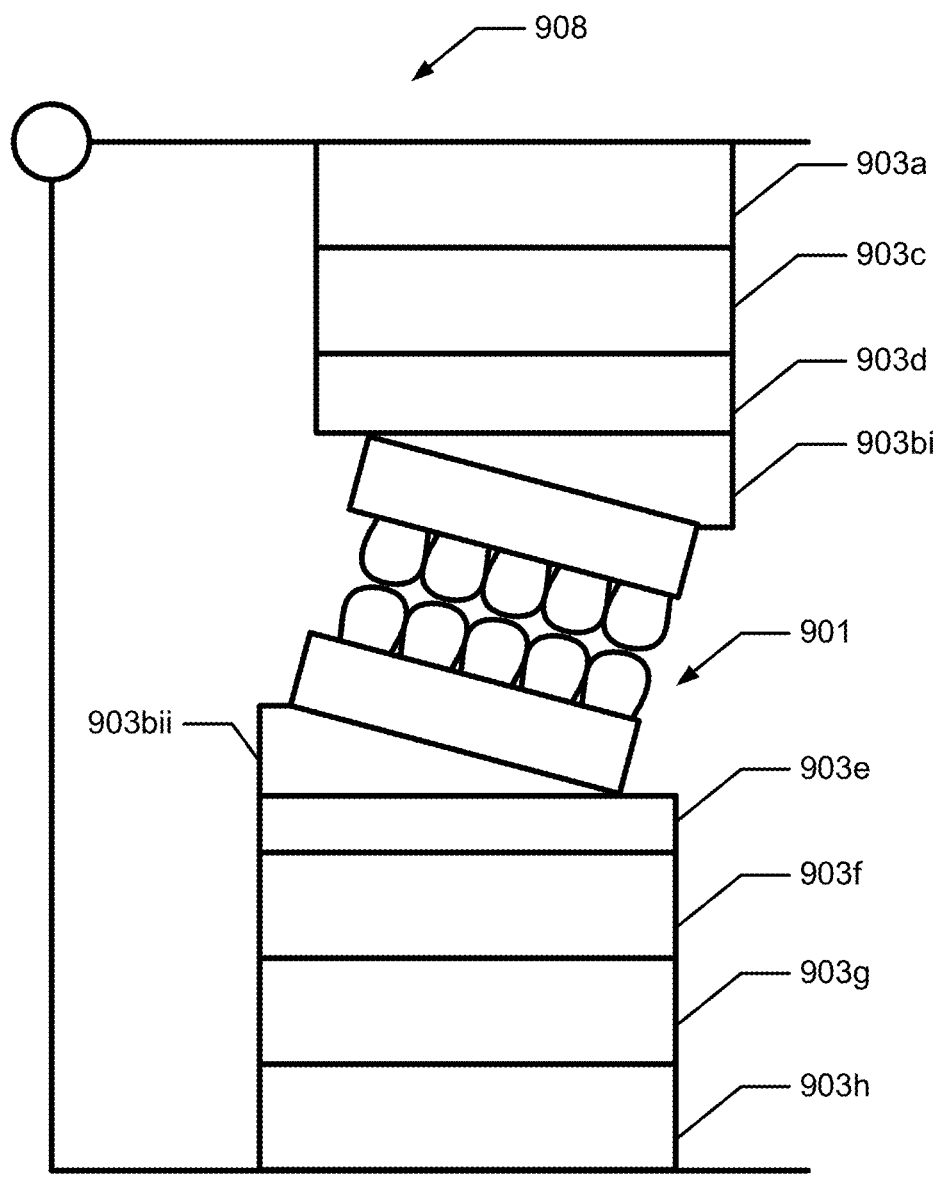

FIG. 9b) shows an example where a dental model 901 is arranged in the articulator 908 by means of a combination of nine spacer elements 903, where two of the spacer elements 903bi and 903bii comprises inclined sides for retaining the inclined dental model 901, and where seven of the spacer elements 903a, 903c, 903d, 903e, 903f, 903g and 903h are rectangular shaped.

Thus there may be any number of spacer elements for retaining the upper and lower part of the dental model in the articulator. However, for stability reasons and accuracy reason it may be an advantage to use as few spacer elements as possible, such as one spacer element for attaching the upper part of the dental model to the upper arm of the articulator and one spacer element for attaching the lower part of the dental model to the lower arm of the articulator. However, if the predefined sizes and heights of the spacer element do not correspond to the distance from the upper part of the dental model to the upper arm of the articulator and/or from the lower part of the dental model to the lower arm of the articulator, extra spacer elements may be used for retaining the dental model.

Alternatively and/or additionally some or all of the spacer elements can comprise an inclined side, be wedge-shaped, triangularly shaped etc.

Figure 10:
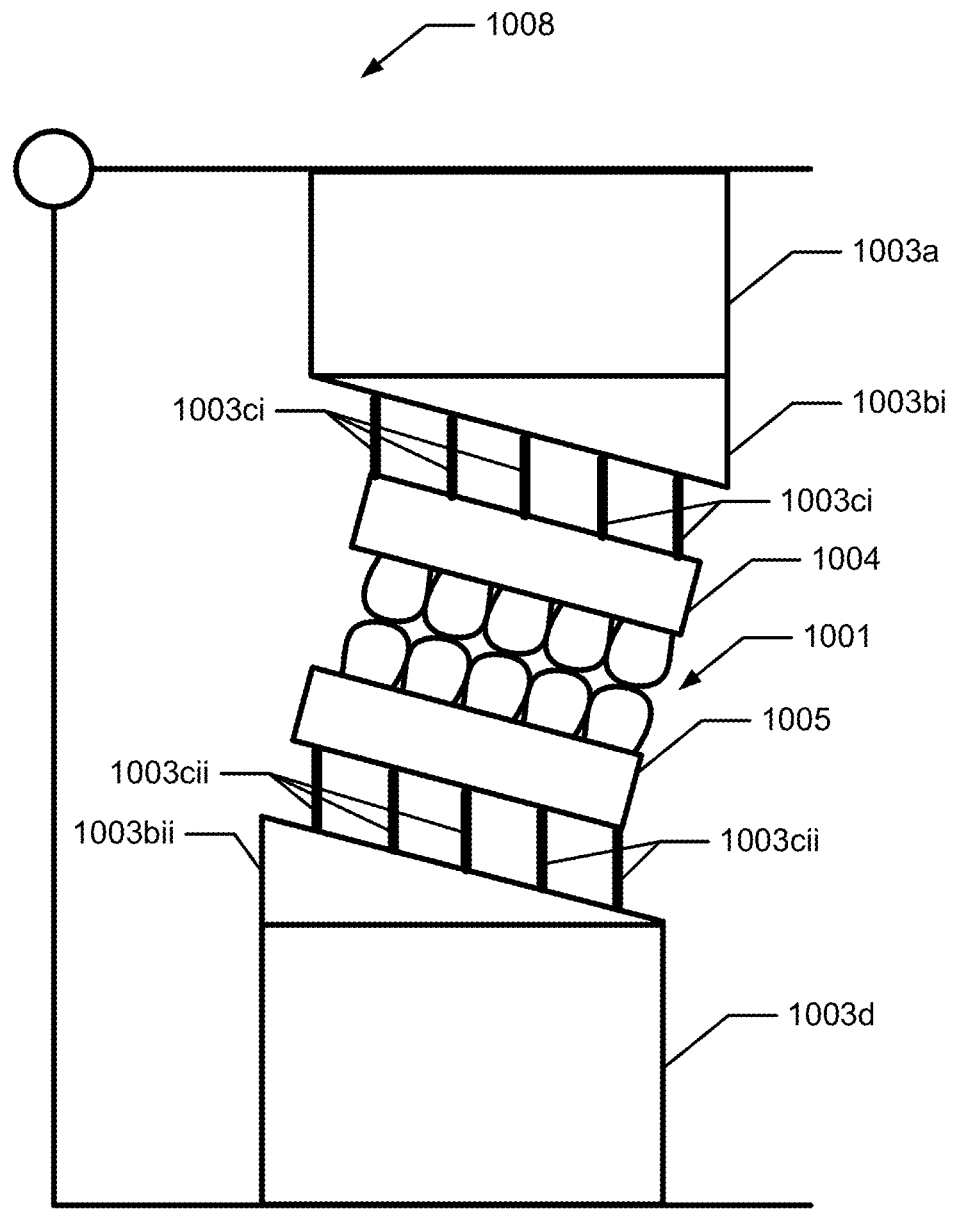
FIG. 10 shows an example where the dental model is attached by means of spacer elements comprising pin shaped spacer elements having a fixed length.

FIG. 10 shows an example where the dental model is attached by means of spacer elements comprising pin shaped spacer elements having a fixed length.

The dental model 1001 is attached in the articulator 1008 by means of a number of different kinds of spacer elements 1003. The spacer elements 1003a and 1003d are rectangular shaped spacer elements. The spacer elements 1003bi and 1003bii are triangular shaped or wedge shaped spacer elements providing that the angle of the dental model in the articulator is different from the horizontal plane. The spacer elements 1003ci and 1003cii are pin shaped spacer elements of the same length or height. In the figure five pin shaped spacer element are shown in connection with both the upper part 1004 of the dental model 1001 and with the lower part 1005 of the model 1001. However, any number of pin shaped spacer elements 1003ci and 1003cii may be used for attaching the dental model 1001.

The effective heights of the pin shaped spacer elements 1003ci and 1003cii are the height of a pin shaped spacer element 1003ci and 1003cii because the pin shaped elements are not build on top of each other. Thus the total effective spacer element height is in this example the height of spacer element 1003a plus the height of spacer element 1003d plus the height of one spacer element 1003ci plus the height of one spacer element 1003cii plus the collective height of spacer elements 1003bi and 1003bii, which in this case is the height of the rectangular block which is created when the two triangular shaped spacer elements are arranged together.

Figure 11:
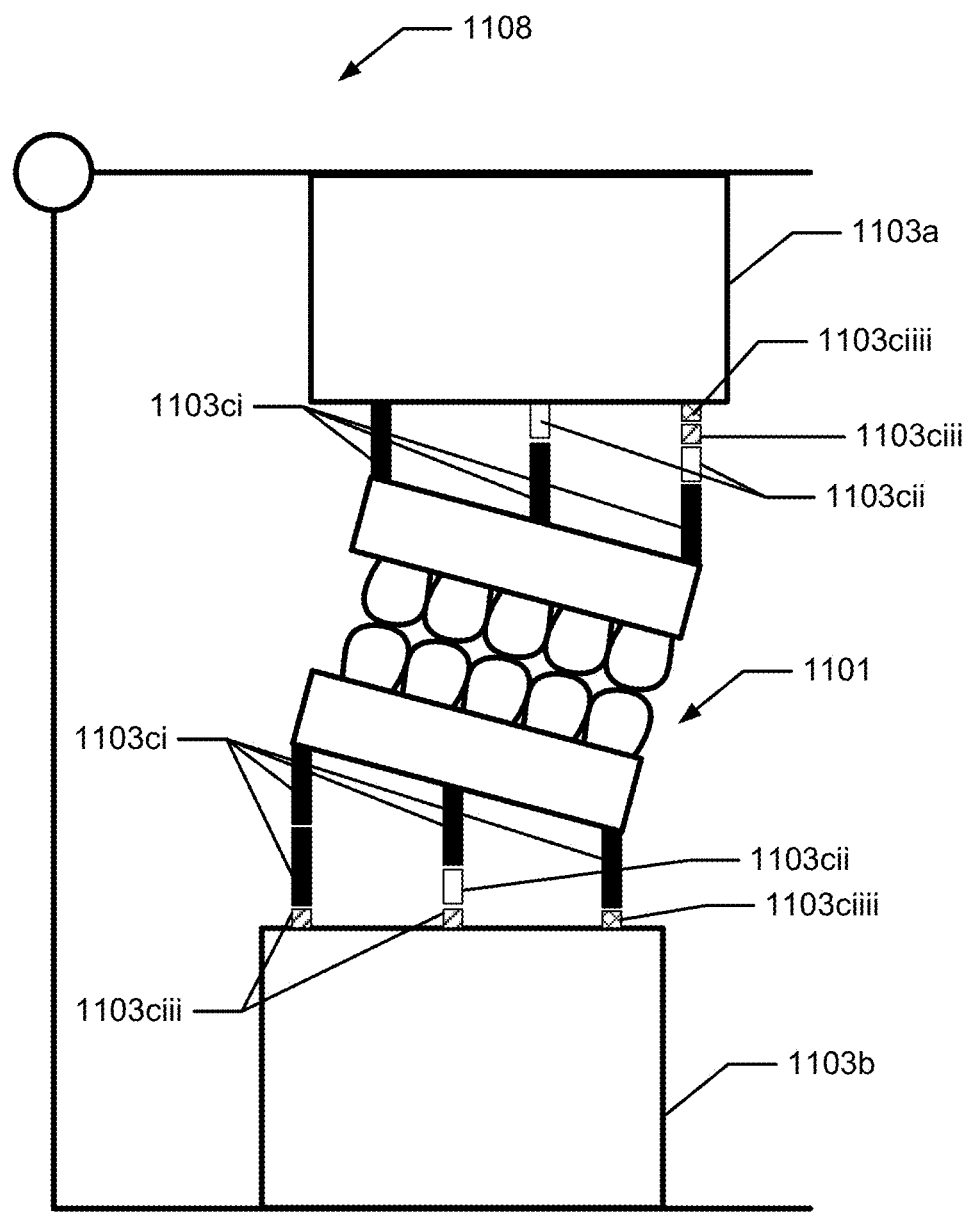
FIG. 11 shows an example where the dental model is attached by means of spacer elements comprising pin shaped spacer elements having a different length.

FIG. 11 shows an example where the dental model is attached by means of spacer elements comprising pin shaped spacer elements having different lengths.

The dental model 1101 is attached in the articulator 1108 by means of a number of different kinds of spacer elements 1103. The spacer elements 1103a and 1103b are rectangular shaped spacer elements. The spacer elements 1103ci, 1103cii, 1103ciii and 1103ciiii are pin shaped spacer elements of different length or heights. When combining the pin shaped spacer elements 1103 having different lengths the angle of the dental model in the articulator can be provided to be different from the horizontal plane of the articulator. In the figure it is shown that three columns of spacer elements are used to attach the lower part and the upper part of the dental model, respectively. Since the dental model is arranged with an angle relative to the horizontal plane of the dental articulator, the total lengths of each of the columns are different, and thus different spacer elements 1103 are used for the attachment. Anything from one spacer element in a column to four spacer elements in a column are shown. However, any number of pin shaped spacer elements 1103c may be used for attaching the dental model 1101.

The total effective heights of the pin shaped spacer elements 1103c may be total height of the shortest pin column on the upper part of the dental model plus the height of the longest pin column on the lower part of the dental model, because the pin shaped elements are build on top of each other, and because the pin shaped columns are arranged in the ends of the dental model.

Thus the total effective spacer element height is in this example the height of spacer element 1003a plus the height of spacer element 1003b plus the height of one spacer element 1003ci, which is the length of the shortest spacer element column on the upper part, plus the total height of two spacer elements 1003ci and the height of one spacer element 1103ciii, which is the length of the longest pin shaped element column on the lower part of the dental model.

However the total effective spacer element height can be calculated in different ways, depending on how the spacer elements are arranged.

FIG. 12 shows examples of the connection elements in the dental model and the spacer elements.

Connection elements may be arranged in the dental model and in the spacer elements for connecting them together. The connection elements can have any shape and size, which is suitable for connecting the upper part and the lower part of the dental model with spacer elements, and/or for connecting individual spacer elements with each other.

Figure 12A:
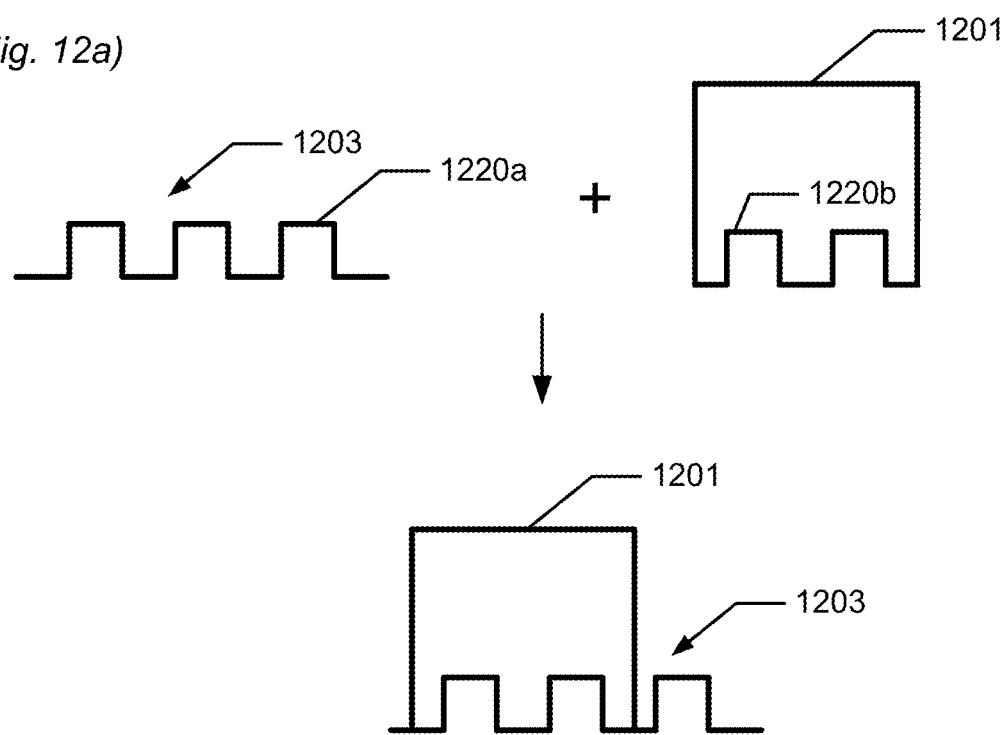
FIG. 12 shows examples of the connection elements in the dental model and the spacer elements.

FIG. 12a shows an example where the connection elements 1220 are quadratic shaped. The connection elements 1220a on the spacer element 1203 match the connection element 1220b on the dental model 1201.

Figure 12B:
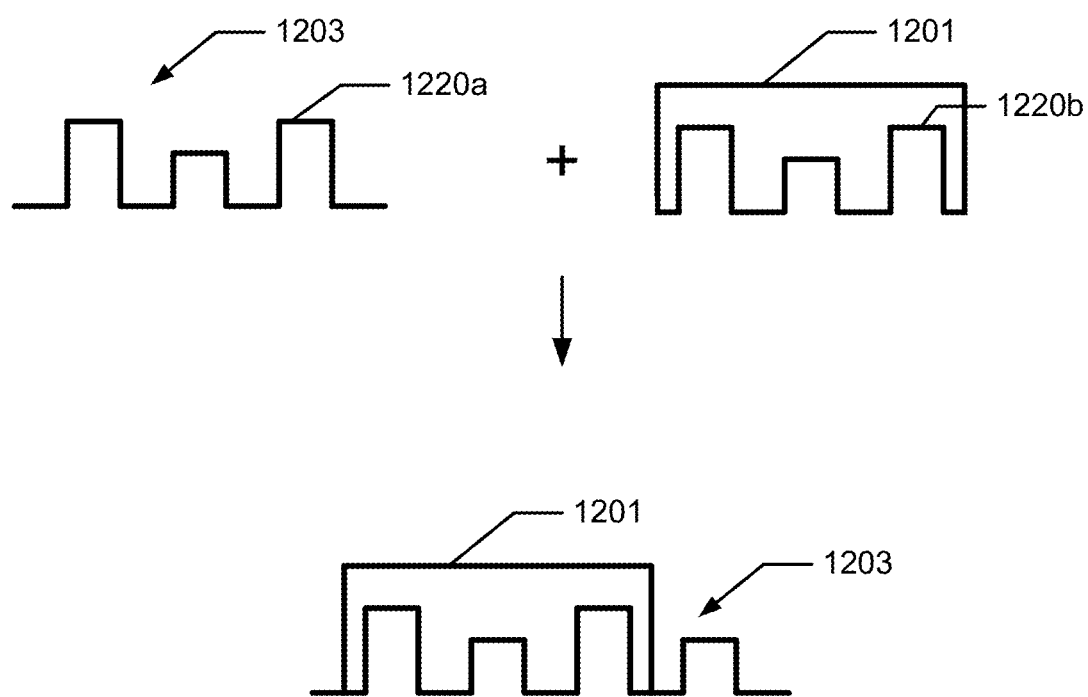

FIG. 12b shows an example where the connection elements are also block shaped or rectangular shaped but where not all connection elements have the same size. The variation in size of the connection elements 1220a on the spacer element 1203 matches the variation in size of the connection element 1220b on the dental model 1201.

The connection elements 1220, where 1220a may indicate the spacer element part of the connection element, and where 1220b may indicate the dental model part of the connection element, can have any shape, size, variation in shape and size, distance between the connection elements etc, which is suitable for connecting two physical items.

FIG. 13 shows examples of different facebows.

A patient's specific facial geometry can be determined by means of traditional facebows or face arches or electronic facebows using electronics and/or optics, where the facebow is attached to e.g. the ears or on the outside of the jaw of the patient. Thus when the patient moves his/her jaws, the face bows measure the movements, and the articulator, e.g. the settings of the articulator, can then be adjusted according to this. Movements may comprise swinging of the jaws, opening of the mouth, dragging of the jaw forward, backwards etc.

A traditional facebow may provide information about static occlusion of a patient, and an electronic facebow may provide information about static and dynamic occlusion.

A conventionel or traditional facebow is a device used in dentistry to record static occlusion, e.g. a device to record the positional relations of the upper arch to the temporomandibular joints and to orient dental casts in this same relationship to the opening axis of the articulator. Thus a facebow may enable gathering of information such that a restoration can be made to the exact cranium/axis relationship of the patient and his/her anatomy. By using a mechanical facial bow with electronic measuring system dynamic occlusion can be measured, and the measurement data can be transmitted by wire or wirelessly to the computer, or saved on a memory component. Thus the data from the electronic facebow measurement can be transferred to the computer for assisting in placing the alignment plane or occlusal plane relative to the virtual model of the teeth.

An example of an electronic facebow is a facebow which enables a precise measurement by means of a number of sensors, such as sound transmitters and microphones. An electronic facebow can measure the lower jaw movements in relation to the patient's cranium. Alternatively, the electronic facebow can be a facebow using magnetic measurement technology, or the facebow can be a facebow which uses ultrasound measurement technology, or the facebow can be any other electronic system transferring the recorded facebow data to a computer.

A facebow may be attached to the head of the patient, e.g. at, above or in the ears, and to the nasal bone between the eyes. A bite fork with impression material on it may then be placed in the patient's mouth touching the teeth in the upper arch, and by means of e.g. ultrasound measurements, the distance between the bite fork and certain points on the facebow may be determined and/or movements of the jaws can be measured. The distance can be used to derive specific anatomical dimensions of the patients face and/or cranium.

Furthermore, another metal fork may then be arranged on the front surface of the teeth in the lower arch, and the patient may move his/her lower jaw into different extreme positions, and by means of e.g. ultrasound measurements, these movements and extreme positions of the lower jaw relative to the facebow may be measured, and by these measurements dynamic occlusion and/or specific anatomical dimensions of the patients face and/or cranium may be determined.

All the measurements of static and/or dynamic occlusion with the facebow as described above may be made and stored electronically, and the measurements may thus be transferred to a computer on which the computer-implemented method of placing the virtual alignment plane relative to the virtual model of the teeth is performed, and thus the dynamic occlusion measured on the patient may be used to perform the placement of the virtual alignment plane relative to the virtual model of the teeth.

Thus the dynamic occlusion can be recorded electronically and played or replayed, while modelling e.g. a restoration.

Figure 13A:
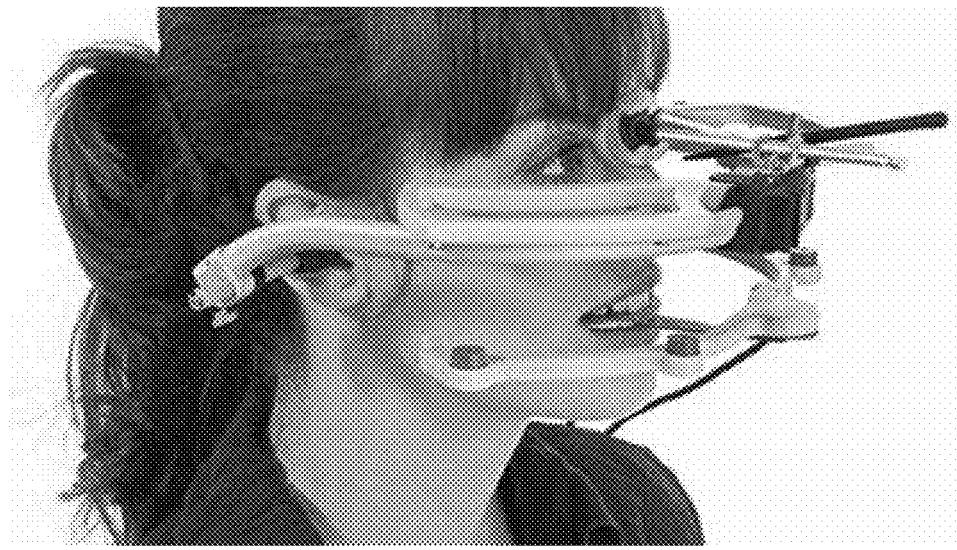
FIG. 13 shows examples of different facebows.
Figure 13B:
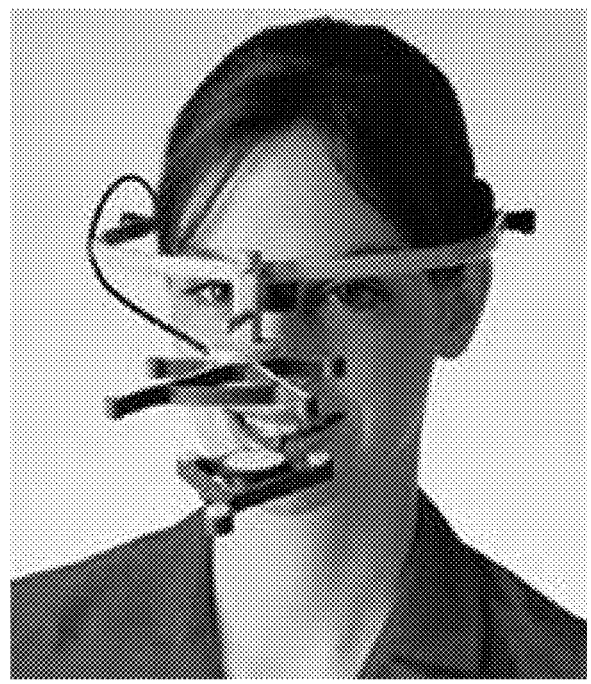
Figure 13C:
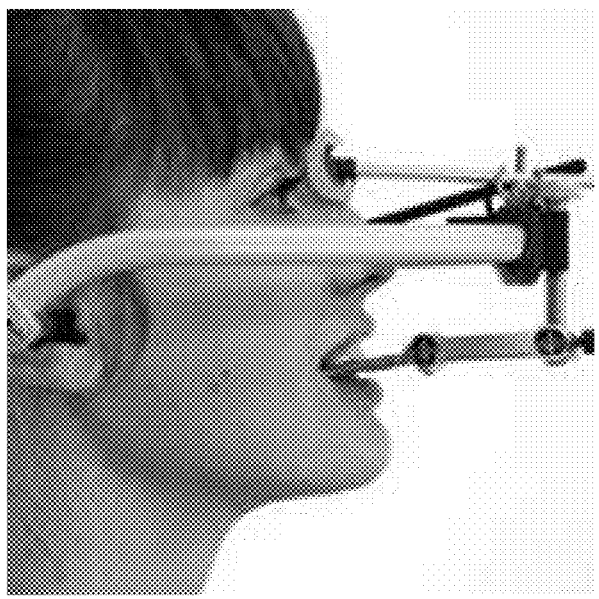
Figure 13D:
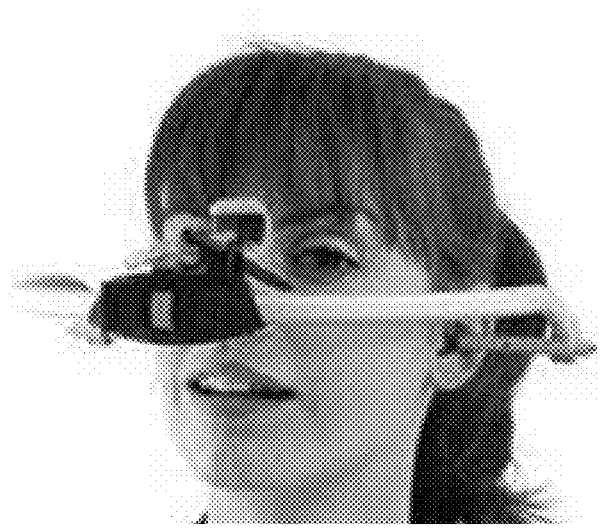

FIGS. 13a) and 13b) are examples of electronic facebows, whereas FIGS. 13c) and 13d) are examples of conventional mechanical facebows.

Figure 14:
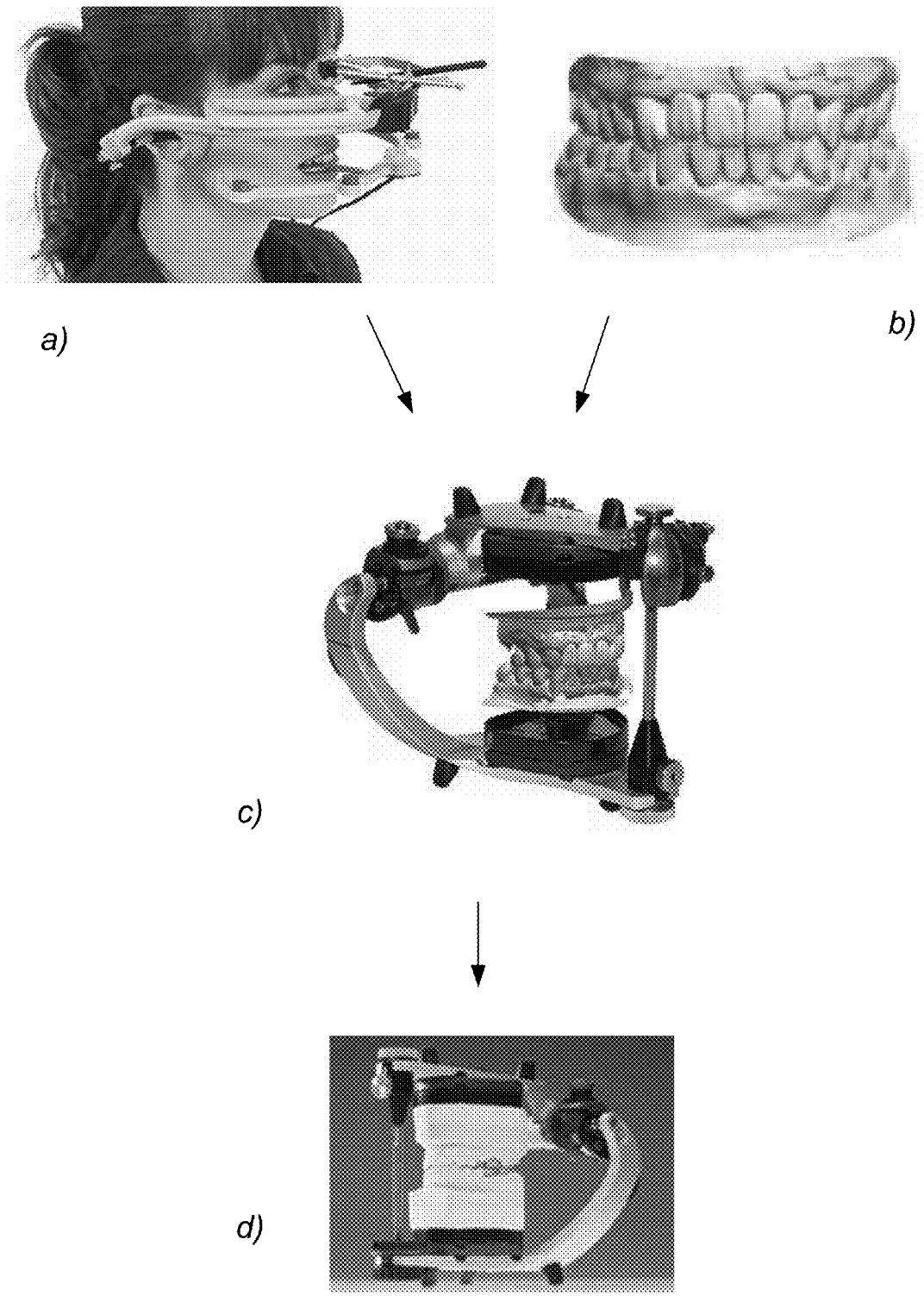
FIG. 14 shows a flowchart of obtaining information for arranging the dental model in the physical articulator.

FIG. 14 shows a flowchart of obtaining information for arranging the dental model in the physical articulator.

In FIG. 14a) an electronic facebow measurement of the patient is made.

In FIG. 14b) a virtual 3D representation which is a virtual 3D dental model of the patient's set of teeth is obtained. The virtual 3D representation may be obtained by direct intra oral scanning of the patient's teeth, or by obtaining a physical impression of the patient's teeth and scanning the impression, or by casting a physical model of the patient's teeth from the physical impression and then scanning the physical model.

In FIG. 14c) the facebow measurement of the patient from FIG. 14a) and the virtual 3D representation or the dental model of the patient's teeth from FIG. 14b) are combined to obtain a virtual arrangement of the virtual dental model in the virtual articulator.

In FIG. 14d) a physical arrangement of the physical dental model in the physical articulator is obtained from the virtual arrangement in FIG. 14c). Note that the dental model is attached in the articulator using traditional means such as gypsum and that the height of the dental model is not minimized in this figure.

Figure 15:
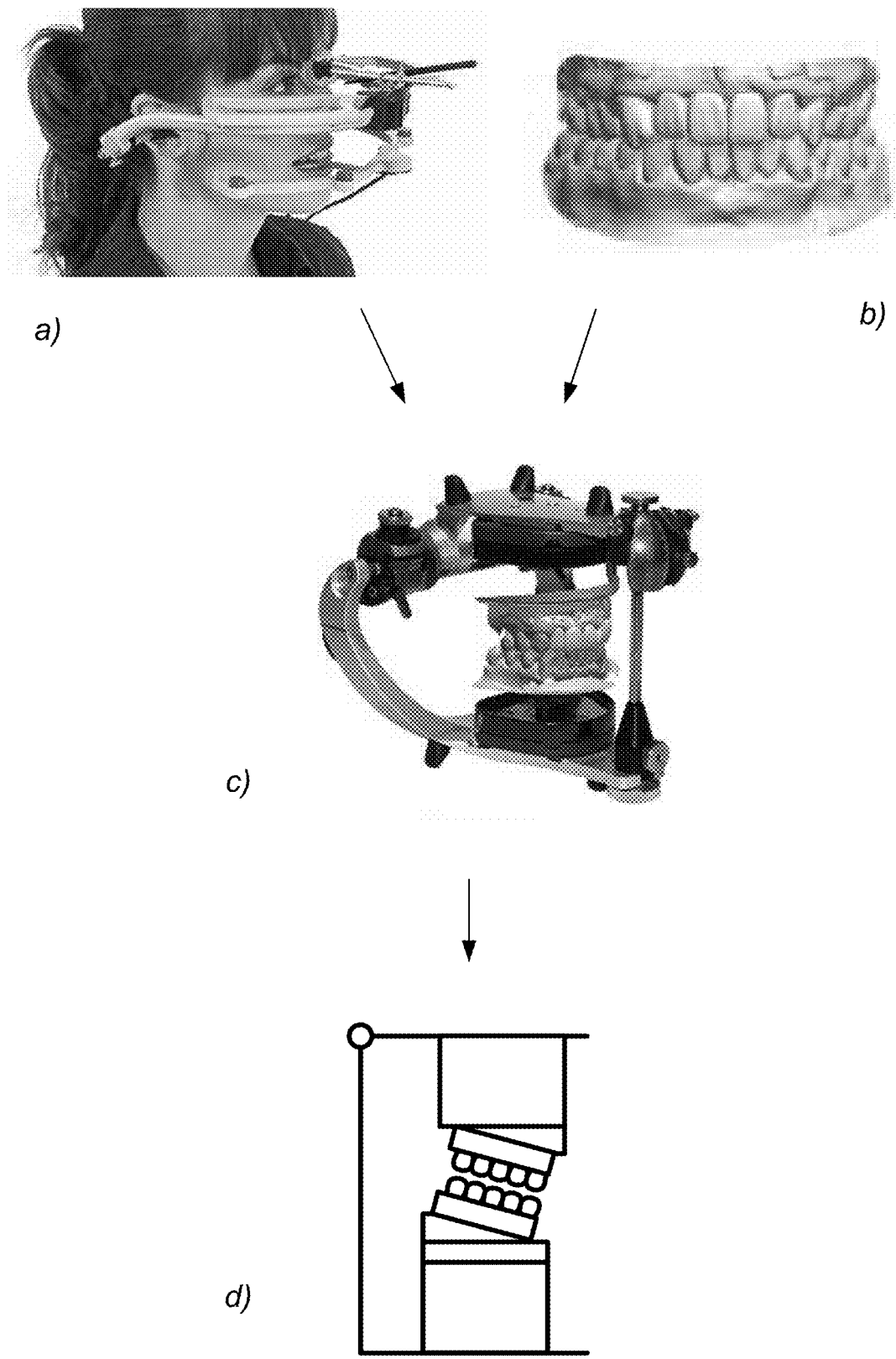
FIG. 15 shows a flowchart of obtaining information for arranging the dental model in the physical articulator.

FIG. 15 shows a flowchart of obtaining information for arranging the dental model in the physical articulator.

In FIG. 15a) an electronic facebow measurement of the patient is made.

In FIG. 15b) a virtual 3D representation which is a virtual 3D dental model of the patient's set of teeth is provided. The virtual 3D representation may be obtained by direct intra oral scanning of the patient's teeth, or by obtaining a physical impression of the patient's teeth and scanning the impression, or by casting a physical model of the patient's teeth from the physical impression and then scanning the physical model.

In FIG. 15c) the facebow measurement of the patient from FIG. 15a) and the virtual 3D representation or the dental model of the patient's teeth from FIG. 15b) are combined to obtain a virtual arrangement of the virtual dental model in the virtual articulator.

In FIG. 15d) a virtual and/or physical arrangement of the dental model in the articulator by means of spacer elements is obtained. The arrangement of the dental model in the articulator is obtained by means of spacer elements, whereby the height of the dental model can be minimized.

FIG. 16 shows a flowchart of obtaining information for arranging a dental model in a virtual articulator.

In FIG. 16a) a mechanical facebow measurement of the patient is made.

In FIG. 16b) the mechanical facebow measurement is used for physically arranging the physical dental model in a physical articulator.

In FIG. 16c) the physical arrangement of the dental model in the physical articulator is used for virtually arranging the virtual dental model in a virtual articulator.

Figure 17:
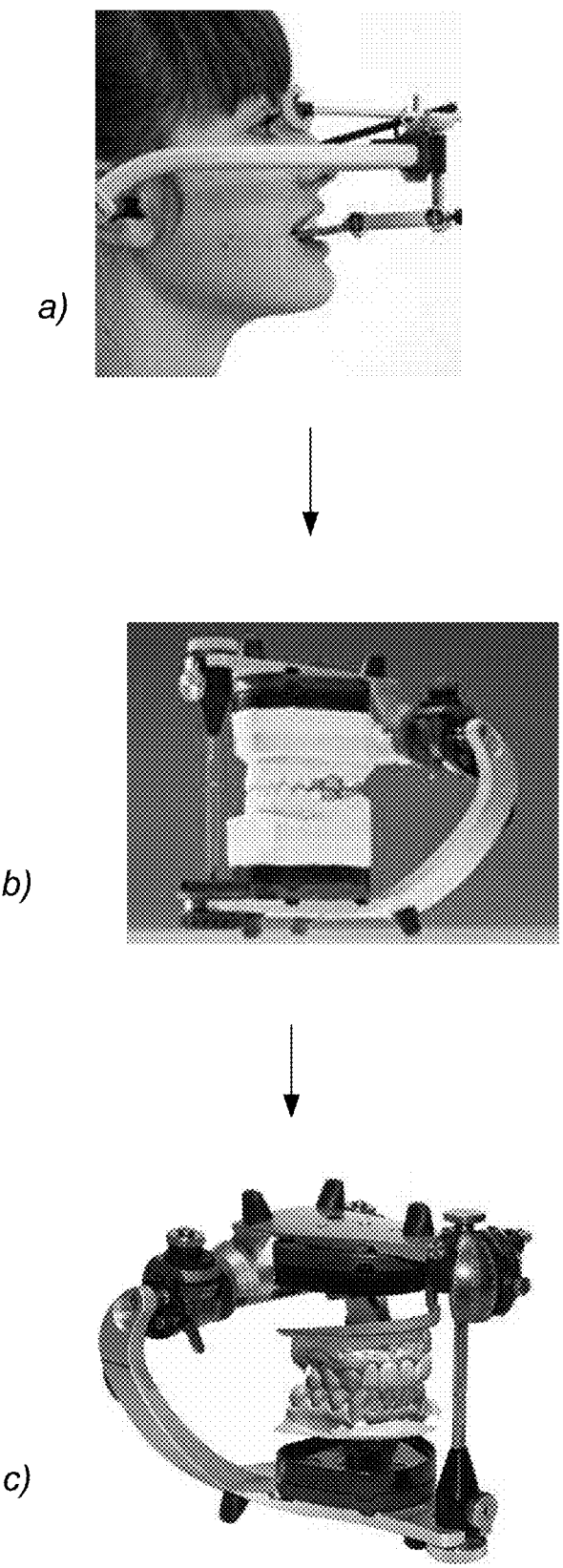
FIG. 17 shows a flowchart of obtaining information for arranging a dental model in a virtual articulator.

FIG. 17 shows a flowchart of obtaining information for arranging a dental model in a virtual articulator.

In FIG. 17a) a mechanical facebow measurement of the patient is made.

In FIG. 17b) the mechanical facebow measurement is used for physically arranging the physical dental model in a physical articulator.

In FIG. 17c) the physical arrangement of the dental model in the physical articulator is used for virtually arranging the virtual dental model in a virtual articulator.

Figure 18:
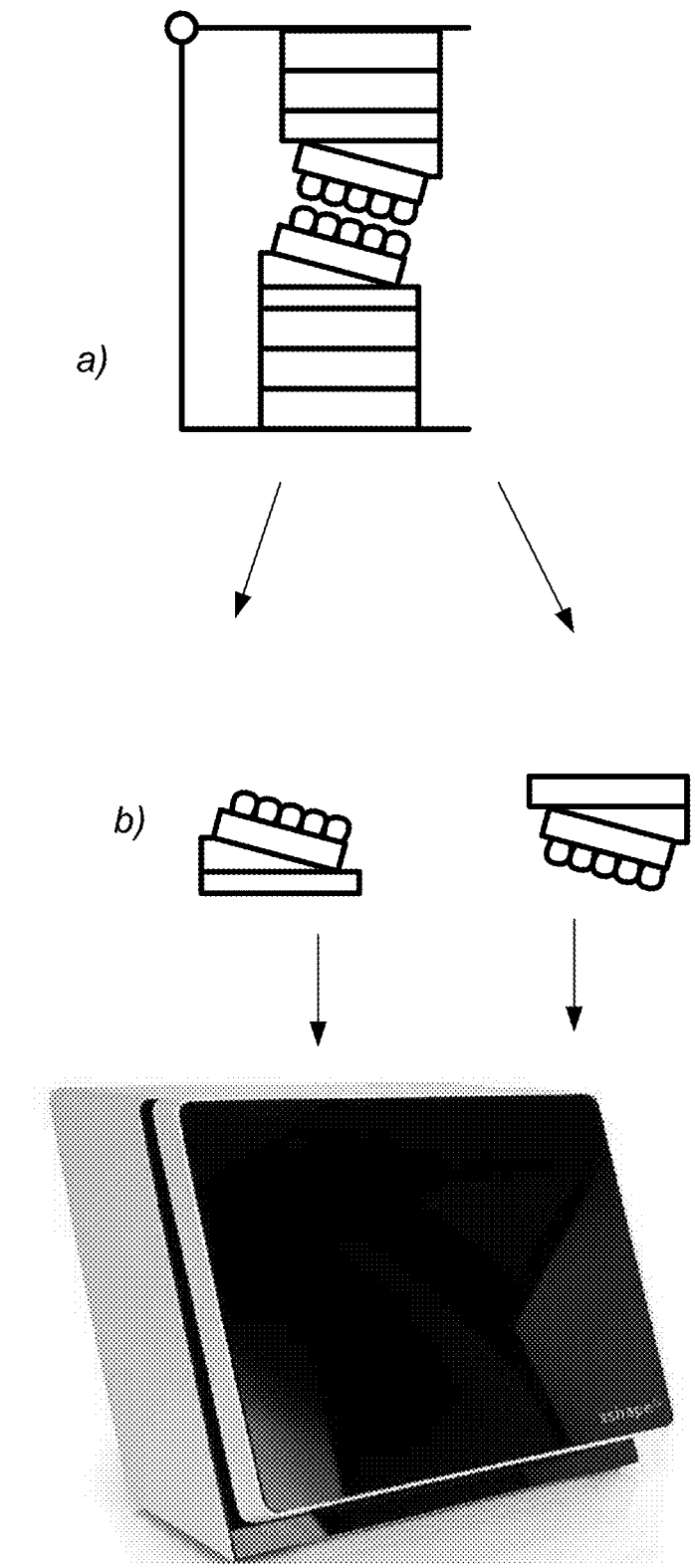
FIG. 18 shows a flowchart of modifying the size of a dental model such that it can be arranged in a desktop scanner for scanning.

FIG. 18 shows a flowchart of modifying the size of a dental model such that it can be arranged in a desktop scanner for scanning.

FIG. 18a) shows an example of a physical dental model physically arranged in a physical articulator by means of a number of spacer elements.

FIG. 18b) shows an example where the dental model is separated in its lower part and upper part. Furthermore only few spacer elements are still attached to the upper and lower part of the dental model so that the upper and lower part are not too high for being arranged and scanned in the desktop scanner.

FIG. 18c) shows that the upper part and lower part of the dental model can be arranged in a desktop scanner to be scanned, since they are low enough for fitting in there. The upper and lower part are low enough because the spacer elements, which are used to attach the dental model in the articulator, can be removed from the dental model when scanning should be performed. If the upper part and lower part of the dental model had been attached in the articulator by means of gypsum, gypsum would have been fixed to the dental model and this gypsum cannot removed, and if too much gypsum was used, the height of the dental model with the fixed gypsum could be too high to fit in the desktop scanner for scanning of the dental model.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method of virtually designing an attachment of a dental model to be manufactured of a patient's set of teeth in a physical dental articulator, where the dental model to be manufactured is to be attached between an upper arm and a lower arm of the physical dental articulator by one or more spacer elements, where the method comprises:
   obtaining a virtual 3D dental model of the patient's set of teeth, wherein the virtual 3D dental model comprises an upper part and a lower part representing a patient's upper jaw and the patient's lower jaw, respectively;
   obtaining a virtual dental articulator corresponding to the physical dental articulator, where the physical dental articulator has a distance between the upper arm and the lower arm in a static position of the physical dental articulator;
   setting or providing the 3D virtual dental model in the virtual dental articulator corresponding to an orientation in which the dental model to be manufactured is intended to be arranged within the physical dental articulator;
   obtaining one or more virtual spacer elements, where each virtual spacer element has a corresponding physical spacer element for attaching the dental model to be manufactured to the physical dental articulator;
   determining a height of the dental model to be manufactured where the height of the dental model to be manufactured is a combined height of a lower and an upper part of the dental model to be manufactured;
   calculating a total height of the physical spacer elements by subtracting the determined height of the dental model to be manufactured from the distance between the upper arm and the lower arm in said static position of the physical dental articulator; and
   determining a combination of physical spacer elements, taking into account a height of each of the physical spacer elements and a number of the physical spacer elements, to obtain the total height of the physical spacer elements calculated in the calculating step, wherein the determined height of the dental model to be manufactured and the total height of the physical spacer elements together equal the distance between the upper arm and the lower arm of the physical dental articulator in said static position.

2. The method according to claim 1, where determining the height of the dental model to be manufactured comprises adjusting a height of the upper and/or lower part of the virtual 3D dental model.

3. The method according to claim 2, wherein the upper and/or lower part of the virtual 3D dental model comprises a base part, and wherein adjusting a height of the virtual 3D dental model comprises adjusting a height of the base of the upper and/or lower part.

4. The method according to claim 1, wherein the method comprises setting a minimum height of the dental model to be manufactured, and where the determined height of the dental model to be manufactured is not less than the minimum height of the dental model to be manufactured.

5. The method according to claim 4, wherein determining the height of the dental model to be manufactured and determining the number of each of the kinds of spacer elements to be used for the attachment of the height of the dental model to be manufactured in the physical dental articulator comprises:
   determining if any combination of spacer elements provides a difference between a height of the physical dental articulator and the minimum height of the dental model to be manufactured;
   if yes, then the difference between the height of the physical dental articulator and the minimum height of the dental model to be manufactured is the total height of the physical spacer elements, and the height of the dental model to be manufactured is equal to the minimum height of the dental model to be manufactured;
   if no, then based on the predetermined heights of the one or more kinds of spacer elements determine a possible total spacer elements height; and then determine the height of the dental model to be manufactured as the difference between the physical dental articulator height and the possible total spacer elements height, under the restriction that the height of the dental model to be manufactured is larger than the minimum height of the dental model to be manufactured.

6. The method according to claim 4, wherein the total height of the physical spacer elements is determined such that the height of the dental model to be manufactured is as close to the minimum height of the dental model to be manufactured as possible.

7. The method according to claim 4, wherein the minimum height of the dental model to be manufactured is determined based on the type of preparation and/or based on the type of pin on the tooth preparation die and/or based on the support means fixing the tooth preparation die in the dental model to be manufactured.

8. The method according to claim 1, wherein the height of the dental model to be manufactured and the total height of the physical spacer elements are determined by an iterative process, where the height of the dental model to be manufactured and the total height of the physical spacer elements are alternately adjusted in steps.

9. The method according to claim 1, wherein a number of different possible total heights of the physical spacer elements are determined based on the predetermined heights of the physical spacer elements.

10. The method according to claim 9, wherein the highest possible total height of the physical spacer elements is selected.

11. The method according to claim 1, wherein at least one of the physical spacer elements is designed to have an inclined surface which compensates for an angle of the patient's occlusion plane relative to the patient's horizontal plane.

12. The method according to claim 1, wherein the height of the dental model to be manufactured is determined with the upper part and the lower part arranged in static occlusion.

13. The method according to claim 1, wherein the physical spacer elements comprise one or more plates, one or more vertical pins, one or more triangular shaped block, one or more blocks with an inclination a side, and/or one or more tripods with individually adjustable height of each the three legs of the tripod.

14. The method according to claim 1, wherein the one or more of the virtual spacer elements are selected from a digital library of spacer elements in different shapes, forms and sizes.

15. The method according to claim 1, wherein the physical spacer elements are standard spacer elements from a manufacturer of spacer elements.

16. The method according to claim 1, wherein one or more of the physical spacer elements are manufactured for the specific dental model.

17. The method according to claim 1, wherein the one or more physical spacer elements and/or the upper part and/or lower part of the dental model comprises one or more connecting elements for connecting the physical spacer elements together and/or for connecting the upper part of the dental model with a physical spacer element and/or for connecting the lower part of the dental model with a physical spacer element.

18. The method according to claim 17, wherein the connecting elements are shaped as protrusions and holes, such that a protrusion in a first physical spacer element and/or in the upper part and/or lower part of the dental model connects with an opposite hole in a second physical spacer element and/or in the lower part and/or upper part of the dental model to be manufactured, respectively.

19. The method according to claim 1, wherein the step of determining the total height of the physical spacer elements and a corresponding height of the dental model to be manufactured and the step of determining the number of each kind of physical spacer elements required to obtain the total height of the spacer elements is performed as one step in which the total height of the physical spacer elements the number of each kind of physical spacer elements required to obtain the total height are determined simultaneously.

20. The method according to claim 1, wherein the virtual 3D dental model is obtained by 3D scanning.

21. The method according to claim 1, further comprising manufacturing the dental model to be manufactured from the virtual 3D model of the patient's set of teeth by direct digital manufacturing.

22. The method according to claim 1, further comprising attaching at least one of the lower part of the virtual 3D dental model with the lower arm or the upper part of the virtual 3D dental model with the upper arm using a plurality of spacer elements.

23. A method of virtually designing an attachment of a dental model to be manufactured of a patient's set of teeth in a physical dental articulator, where the method comprises:
obtaining a virtual 3D dental model of the patient's set of teeth;
obtaining a virtual dental articulator corresponding to the physical dental articulator, where the physical dental articulator comprises an upper arm and a lower arm and has a known distance between the upper arm and the lower arm in a static position of the physical dental articulator;
setting or providing the 3D virtual dental model in the virtual dental articulator corresponding to an orientation which the dental model to be manufactured is intended to be arranged within the physical dental articulator;
setting an initial height of the 3D virtual dental model;
providing one or more virtual spacer elements with pre-determined heights, where each kind of the virtual spacer elements has a corresponding physical spacer element;
where the total height of the physical spacer elements is a combined height of all the physical spacer elements used for attaching the dental model to be manufactured in the physical dental articulator; such that a height of the dental model to be manufactured and the total height of the physical spacer elements equal the distance between the upper arm and the lower arm of the physical dental articulator, whereby the dental model to be manufactured is adapted to be attached between the upper arm and the lower arm in the physical dental articulator by the one or more kinds of physical spacer elements;
applying the height of the dental model to be manufactured and the distance between the upper arm and the lower arm in said static position of the physical dental articulator to calculate an initial total height of the physical spacer elements by calculating a difference between the physical dental articulator height and the height of the dental model;
determining if any combination and/or number of the physical spacer elements provides the initial total height of the physical spacer elements;
if no combination and/or number of the different kinds of physical spacer elements provides the initial total height of the physical spacer elements, then:
calculate an adjusted total height of the physical spacer elements, which is possible to obtain using the physical spacer elements; and
calculate an adjusted height of the dental model to be manufactured, such that the height of the dental model to be manufactured and the adjusted total height of the physical spacer elements equal the distance between the upper arm and the lower arm of the physical dental articulator.

24. The method according to claim 23, wherein the virtual 3D dental model is obtained by 3D scanning.

25. The method according to claim 23, further comprising manufacturing the dental model to be manufactured from the virtual 3D model of the patient's set of teeth by direct digital manufacturing.

26. A method of virtually designing an attachment of a dental model to be manufactured of a patient's set of teeth in a physical dental articulator, where the dental model to be manufactured is to be attached between an upper arm and a lower arm of the physical dental articulator by one or more spacer elements, where the method comprises:
obtaining a virtual 3D dental model of the patient's set of teeth, wherein the virtual 3D dental model comprises an upper part and a lower part representing a patient's upper jaw and the patient's lower jaw, respectively;
obtaining a virtual dental articulator corresponding to the physical dental articulator, where the physical dental articulator has a distance between the upper arm and the lower arm in a static position of the physical dental articulator;
setting or providing the 3D virtual dental model in the virtual dental articulator corresponding to an orientation in which the dental model to be manufactured is intended to be arranged within the physical dental articulator;
obtaining one or more virtual spacer elements, where each virtual spacer element has a corresponding physical spacer element for attaching the dental model to be manufactured to the physical articulator;
determining a height of the dental model to be manufactured, where the height of the dental model to be manufactured is a combined height of a lower and an upper part of the dental model to be manufactured;
calculating a total height of the physical spacer elements by adding (1) a distance between the upper arm of the physical dental articulator and a lowest part of the upper part and (2) a distance between the lower arm of the physical dental articulator and a highest part of the lower part; and determining a combination of physical spacer elements, taking into account a height of each of the physical spacer elements and a number of the physical spacer elements, to obtain the total height of the physical spacer elements calculated in the calculating step, wherein a projected height of the dental model to be manufactured onto a vertical axis of the articulator and the calculated total height of the physical spacer elements without inclusion of height of at least one spacer element that overlaps with the height of the dental model when the dental model is arranged in the articulator together equal the distance between the upper arm and the lower arm of the physical dental articulator in said static position;

wherein:

the orientation comprises an angle of an occlusion plane of the 3D virtual dental model relative to a horizontal plane of the virtual dental articulator such that the 3D virtual dental model is inclined relative to the horizontal plane when arranged in the virtual dental articulator.

* * * * *